US012393272B2

(12) United States Patent
Forsland et al.

(10) Patent No.: US 12,393,272 B2
(45) Date of Patent: Aug. 19, 2025

(54) BRAIN COMPUTER INTERFACE FOR AUGMENTED REALITY

(71) Applicant: Cognixion Corporation, Santa Barbara, CA (US)

(72) Inventors: Andreas Forsland, Santa Barbara, CA (US); Leonard Zerman, Santa Barbara, CA (US)

(73) Assignee: Cognixion Corporation, Santa Barbara, CA (US)

( * ) Notice: Subject to any disclaimer, the term of this patent is extended or adjusted under 35 U.S.C. 154(b) by 0 days.

(21) Appl. No.: 17/848,263

(22) Filed: Jun. 23, 2022

(65) Prior Publication Data

US 2022/0326772 A1    Oct. 13, 2022

Related U.S. Application Data

(63) Continuation of application No. 17/222,897, filed on Apr. 5, 2021, now Pat. No. 11,402,909, which is a
(Continued)

(51) Int. Cl.
*G06F 3/01*    (2006.01)
*G06F 3/023*   (2006.01)
(Continued)

(52) U.S. Cl.
CPC ............ *G06F 3/015* (2013.01); *G06F 3/016* (2013.01); *G06F 3/023* (2013.01); *G06F 3/14* (2013.01);
(Continued)

(58) Field of Classification Search
None
See application file for complete search history.

(56) References Cited

U.S. PATENT DOCUMENTS

| 5,252,951 A | 10/1993 | Tannenbaum et al. |
| 5,659,764 A | 8/1997 | Sakiyama et al. |

(Continued)

FOREIGN PATENT DOCUMENTS

JP    2017126337 A    7/2017

OTHER PUBLICATIONS

U.S. Appl. No. 15/498,158, filed Apr. 26, 2017, Andreas Forsland.
(Continued)

*Primary Examiner* — Nicholas J Lee
(74) *Attorney, Agent, or Firm* — Carnelian Law

(57) ABSTRACT

An apparatus, system, and method of a brain computer interface in a headset including an augmented reality display, one or more sensors, a processing module, at least one biofeedback device, and a battery. The interface may include a printed circuit board that has the sensors to read bio-signals, provides biofeedback, and performs the processing, analyzing, and mapping of bio-signals into output. The output provides feedback via stimulation of multiple sensory brain systems of a user, including audio and visual on the augmented reality display, or audio and haptic in terms of vibration patterns that a human user may feel. All together this forms a closed-loop system, by detecting the bio-signal, then providing sensory-feedback, which in turn enhances the bio-signal.

31 Claims, 25 Drawing Sheets

Related U.S. Application Data continuation-in-part of application No. 17/141,162, filed on Jan. 4, 2021, now Pat. No. 11,237,635, and a continuation-in-part of application No. 16/749,892, filed on Jan. 22, 2020, now abandoned, said application No. 17/141,162 is a continuation-in-part of application No. 15/929,085, filed on Jan. 9, 2019, now Pat. No. 10,990,175, said application No. 17/222,897 is a continuation-in-part of application No. 15/498,158, filed on Apr. 26, 2017, now abandoned.

(60) Provisional application No. 62/704,048, filed on Jan. 22, 2019, provisional application No. 62/752,133, filed on Oct. 29, 2018.

(51) Int. Cl.
  G06F 3/14 (2006.01)
  G06F 3/16 (2006.01)
  G06N 5/02 (2023.01)
  G06N 20/00 (2019.01)
  A61B 5/00 (2006.01)
  H04W 84/18 (2009.01)

(52) U.S. Cl.
  CPC ............... *G06F 3/16* (2013.01); *G06N 5/02* (2013.01); *G06N 20/00* (2019.01); *A61B 5/0075* (2013.01); *H04W 84/18* (2013.01)

(56) References Cited

U.S. PATENT DOCUMENTS

| | | | |
|---|---|---|---|
| 5,777,614 | A | 7/1998 | Ando et al. |
| 6,154,758 | A | 11/2000 | Chiang |
| 6,243,683 | B1 | 6/2001 | Peters |
| 6,327,566 | B1 | 12/2001 | Vanbuskirk et al. |
| 6,801,897 | B2 | 10/2004 | Kist et al. |
| 7,039,676 | B1 | 5/2006 | Day et al. |
| 7,447,635 | B1 | 11/2008 | Konopka et al. |
| 7,565,295 | B1 | 7/2009 | Hernandez-Rebollar |
| 7,809,550 | B1 | 10/2010 | Barrows |
| 8,175,728 | B2 | 5/2012 | Weinberg et al. |
| 8,335,694 | B2 | 12/2012 | Reiner |
| 8,676,175 | B2 | 3/2014 | Cheng et al. |
| 8,745,541 | B2 | 6/2014 | Wilson et al. |
| 8,793,137 | B1 | 7/2014 | Roy et al. |
| 8,854,433 | B1 | 10/2014 | Rafii |
| 9,052,817 | B2 | 6/2015 | Hotelling |
| 9,069,386 | B2 | 6/2015 | Ajika |
| 9,165,159 | B1 | 10/2015 | McDonnell |
| 9,175,728 | B2 | 11/2015 | White |
| 9,223,537 | B2 | 12/2015 | Brown et al. |
| 9,280,229 | B2 | 3/2016 | Duffield |
| 9,280,366 | B2 | 3/2016 | Kamal et al. |
| 9,304,593 | B2 | 4/2016 | Cohen et al. |
| 9,477,642 | B2 | 10/2016 | Decker et al. |
| 9,489,051 | B2 | 11/2016 | Mankowski et al. |
| 9,489,081 | B2 | 11/2016 | Anzures et al. |
| 9,495,128 | B1 | 11/2016 | Ledet |
| 9,524,272 | B2 | 12/2016 | Decker et al. |
| 9,529,440 | B2 | 12/2016 | Piemonte et al. |
| 9,582,246 | B2 | 2/2017 | Klein et al. |
| 9,600,169 | B2 | 3/2017 | Sa et al. |
| 9,606,647 | B1 | 3/2017 | Spencer-Harper et al. |
| 9,710,657 | B1 | 7/2017 | Kakkar et al. |
| 9,830,311 | B2 | 11/2017 | Zhai et al. |
| 10,013,601 | B2 | 7/2018 | Ebersman et al. |
| 10,025,776 | B1 | 7/2018 | Sjoberg et al. |
| 10,158,609 | B2 | 12/2018 | Lim et al. |
| 10,210,002 | B2 | 2/2019 | Zheng |
| 10,311,144 | B2 | 6/2019 | Bellegarda et al. |
| 10,338,637 | B1 | 7/2019 | Bristol et al. |
| 10,770,092 | B1 | 9/2020 | Adams et al. |
| 10,990,175 | B2 | 4/2021 | Forsland et al. |
| 11,266,342 | B2 | 3/2022 | Huggins et al. |
| 2003/0055644 | A1 | 3/2003 | Johnston et al. |
| 2004/0005092 | A1 | 1/2004 | Tomasi |
| 2004/0037540 | A1 | 2/2004 | Frohlich et al. |
| 2004/0191744 | A1 | 9/2004 | Guirguis |
| 2005/0038663 | A1 | 2/2005 | Brotz |
| 2006/0066509 | A1* | 3/2006 | Gross ............... G06F 3/01 345/8 |
| 2006/0107238 | A1 | 5/2006 | Gold |
| 2007/0279315 | A1 | 12/2007 | Laves et al. |
| 2007/0284448 | A1 | 12/2007 | Wang |
| 2008/0104547 | A1 | 5/2008 | Morita et al. |
| 2008/0154604 | A1 | 6/2008 | Sathish et al. |
| 2010/0050134 | A1 | 2/2010 | Clarkson |
| 2010/0123724 | A1 | 5/2010 | Moore et al. |
| 2010/0179864 | A1 | 7/2010 | Feldman et al. |
| 2011/0043662 | A1 | 2/2011 | Kim |
| 2011/0050594 | A1 | 3/2011 | Kim et al. |
| 2011/0302538 | A1 | 12/2011 | Vennelakanti et al. |
| 2011/0313768 | A1 | 12/2011 | Klein et al. |
| 2012/0026290 | A1 | 2/2012 | Lim et al. |
| 2012/0035934 | A1 | 2/2012 | Cunningham |
| 2012/0038550 | A1 | 2/2012 | Lemmey et al. |
| 2012/0108997 | A1* | 5/2012 | Guan ............... A61B 5/374 600/545 |
| 2012/0162350 | A1 | 6/2012 | Lee et al. |
| 2012/0182288 | A1 | 7/2012 | Williams et al. |
| 2012/0268294 | A1 | 10/2012 | Michaelis et al. |
| 2012/0268399 | A1 | 10/2012 | Cheng et al. |
| 2012/0327023 | A1 | 12/2012 | Fleizach |
| 2013/0041654 | A1 | 2/2013 | Walker et al. |
| 2013/0054693 | A1 | 2/2013 | Chennamadhavuni |
| 2013/0074014 | A1 | 3/2013 | Ouyang et al. |
| 2013/0144629 | A1 | 6/2013 | Johnston et al. |
| 2013/0147933 | A1 | 6/2013 | Kulas |
| 2013/0257781 | A1 | 10/2013 | Phulwani et al. |
| 2013/0259238 | A1 | 10/2013 | Xiang et al. |
| 2013/0285922 | A1 | 10/2013 | Alberth, Jr. et al. |
| 2013/0339850 | A1 | 12/2013 | Hardi et al. |
| 2014/0026101 | A1 | 1/2014 | Pallakoff et al. |
| 2014/0067397 | A1 | 3/2014 | Radebaugh |
| 2014/0075286 | A1 | 3/2014 | Harada |
| 2014/0082694 | A1 | 3/2014 | Sanghavi |
| 2014/0143683 | A1 | 5/2014 | Underwood, IV et al. |
| 2014/0149987 | A1 | 5/2014 | Barillari et al. |
| 2014/0171036 | A1 | 6/2014 | Simmons |
| 2014/0201024 | A1 | 7/2014 | Collier et al. |
| 2014/0234809 | A1 | 8/2014 | Colvard |
| 2014/0267094 | A1 | 9/2014 | Hwang et al. |
| 2014/0267543 | A1 | 9/2014 | Kerger et al. |
| 2014/0278368 | A1 | 9/2014 | Skory et al. |
| 2014/0303960 | A1 | 10/2014 | Orsini et al. |
| 2014/0325360 | A1 | 10/2014 | Jung et al. |
| 2014/0330951 | A1 | 11/2014 | Sukoff et al. |
| 2014/0333529 | A1* | 11/2014 | Kim ............... G06F 3/015 345/156 |
| 2014/0342667 | A1 | 11/2014 | Aarnio |
| 2014/0347265 | A1 | 11/2014 | Aimone et al. |
| 2015/0002549 | A1 | 1/2015 | Park et al. |
| 2015/0006172 | A1 | 1/2015 | Alameh |
| 2015/0022328 | A1 | 1/2015 | Choudhury |
| 2015/0033126 | A1 | 1/2015 | Shin |
| 2015/0065182 | A1 | 3/2015 | Adams |
| 2015/0102903 | A1 | 4/2015 | Wilkinson |
| 2015/0109193 | A1 | 4/2015 | Sly et al. |
| 2015/0169169 | A1 | 6/2015 | Andersson |
| 2015/0185996 | A1* | 7/2015 | Brown ............... G06F 3/04817 715/706 |
| 2015/0199320 | A1 | 7/2015 | Ho et al. |
| 2015/0212676 | A1 | 7/2015 | Khare |
| 2015/0220774 | A1 | 8/2015 | Ebersman et al. |
| 2015/0241969 | A1 | 8/2015 | Elangovan et al. |
| 2015/0293996 | A1 | 10/2015 | Liu |
| 2015/0302851 | A1 | 10/2015 | Talwar et al. |
| 2015/0363001 | A1 | 12/2015 | Malzbender |
| 2016/0026252 | A1 | 1/2016 | McCoy et al. |
| 2016/0055232 | A1 | 2/2016 | Yang et al. |
| 2016/0062540 | A1 | 3/2016 | Yang et al. |
| 2016/0077547 | A1 | 3/2016 | Aimone et al. |

(56) References Cited

U.S. PATENT DOCUMENTS

| | | |
|---|---|---|
| 2016/0109954 A1 | 4/2016 | Harris et al. |
| 2016/0117147 A1 | 4/2016 | Zambetti et al. |
| 2016/0179908 A1 | 6/2016 | Johnston et al. |
| 2016/0234551 A1 | 8/2016 | Allegretti et al. |
| 2016/0239084 A1 | 8/2016 | Connor et al. |
| 2016/0242623 A1 | 8/2016 | Pasini et al. |
| 2016/0246929 A1 | 8/2016 | Zenati et al. |
| 2016/0277903 A1 | 9/2016 | Poosala et al. |
| 2016/0292217 A1 | 10/2016 | Sinha et al. |
| 2016/0325108 A1 | 11/2016 | Volpe et al. |
| 2016/0371917 A1 | 12/2016 | Yang et al. |
| 2017/0060850 A1 | 3/2017 | Lewis et al. |
| 2017/0083586 A1 | 3/2017 | Huang et al. |
| 2017/0098122 A1 | 4/2017 | Kaliouby et al. |
| 2017/0127129 A1 | 5/2017 | Ivanov et al. |
| 2017/0140563 A1 | 5/2017 | No et al. |
| 2017/0262045 A1 | 9/2017 | Rouvinez et al. |
| 2017/0263248 A1 | 9/2017 | Gruber et al. |
| 2017/0336926 A1 | 11/2017 | Chaudhri et al. |
| 2017/0365101 A1* | 12/2017 | Samec ............... A61B 5/4082 |
| 2018/0024651 A1 | 1/2018 | Haran et al. |
| 2018/0130459 A1 | 5/2018 | Paradiso et al. |
| 2018/0133900 A1 | 5/2018 | Breazeal et al. |
| 2018/0173323 A1 | 6/2018 | Harvey et al. |
| 2018/0188807 A1* | 7/2018 | Cimenser ............... A61B 5/18 |
| 2018/0193589 A1 | 7/2018 | Mclaughlin et al. |
| 2018/0217382 A1 | 8/2018 | Urbach et al. |
| 2018/0239430 A1 | 8/2018 | Tadi et al. |
| 2018/0330732 A1 | 11/2018 | Dasgupta |
| 2018/0336891 A1 | 11/2018 | Sun et al. |
| 2018/0343024 A1 | 11/2018 | Sahebjavaher et al. |
| 2019/0005021 A1 | 1/2019 | Miller et al. |
| 2019/0005024 A1 | 1/2019 | Somech et al. |
| 2019/0007732 A1 | 1/2019 | Havinal |
| 2019/0187782 A1* | 6/2019 | Liu ................... H04M 3/42161 |
| 2019/0307350 A1 | 10/2019 | Sridhar et al. |
| 2020/0022577 A1* | 1/2020 | Rishoni ................ A61B 3/032 |
| 2020/0050236 A1 | 2/2020 | Lin et al. |
| 2020/0193965 A1 | 6/2020 | Cordell et al. |
| 2020/0267936 A1 | 8/2020 | Tran |
| 2020/0301968 A1 | 9/2020 | Huang et al. |

OTHER PUBLICATIONS

U.S. Appl. No. 17/141,162, filed Jan. 2021, Forsland.
U.S. Appl. No. 63/170,987, filed Apr. 2021, Ravi.
PCT/US19/58640_ISA210_International_Search_Report_Jan. 24, 2020.
PCT/US19/58640_Written_Opinion_Jan. 24, 2020.
Angrisani Leopoldo et al: "Wearable Augmented Reality and Brain Computer Interface to Improve Human-Robot Interactions in Smart Industry: A Feasibility Study for SSVEP Signals", 2018 IEEE 4th International Forum on Research and Technology for Society and Industry {RTSI), IEEE, Sep. 10, 2018 {Sep. 10, 2018), pp. 1-5, XP033459129.
Seungchan Lee et al: "Review of Wireless Brain-Computer Interface Systems" In: "Brain-Computer Interface Systems—Recent Progress and Future Prospects", Jun. 5, 2013 {Jun. 5, 2013), InTech, XP055282587, ISBN: 978-953-51-1134-4, pp. 215-238, DOI: 10.5772/56436.
English Translation of Office Action of Japan Patent Office, Mailing Date: Mar. 18, 2025.

* cited by examiner

BRAIN COMPUTER INTERFACE FOR AUGMENTED REALITY

CROSS-REFERENCE TO RELATED APPLICATIONS

This application is a continuation-in-part of U.S. Non-provisional patent application Ser. No. 15/929,085, filed on Jan. 9, 2019, which claims the benefit of U.S. provisional patent application Ser. No. 62/752,133, filed on Oct. 29, 2018, and is a continuation-in-part of U.S. Non-provisional patent application Ser. No. 17/141,162, filed Jan. 4, 2021, which is a continuation-in-part of:

U.S. patent application Ser. No. 15/498,158, filed Apr. 26, 2017, entitled "Gesture Recognition Communication System"; U.S. patent application Ser. No. 16/749,892, filed Jan. 22, 2020, entitled "CONTEXT AWARE DUAL DISPLAY TO AUGMENT REALITY," which claims priority from Provisional application No. 62/704,048, filed on Jan. 22, 2019; and U.S. patent application Ser. No. 15/929,085, filed Jan. 9, 2019, entitled "BRAIN COMPUTER INTERFACE FOR AUGMENTED REALITY" which claims priority from Provisional application No. 62/752,133, filed on Oct. 29, 2018; each of which is incorporated herein by reference in its entirety.

BACKGROUND

When typical brain-computer interfaces (BCIs) are used, an external device or a computer and monitor are required to process and act upon the brain signals from the BCI. This typically but not always requires a wired connection between BCI, and a variety of separate systems and devices for processing data, as well as displaying and synchronizing visual information with the BCI. Usually, the devices used for the brain-computer interface may require multiple dangling wires, which present multiple points of failure in the sense that if any of those wires are damaged, the brain-computer interface may fail to function. Typically, setting up a BCI system is time intensive and mostly location dependent in a room or lab. Additionally, there is a delay in receiving feedback based on the bio-signal from the brain, and another human may be required to be present in order to read the results from a separate device.

In addition to these problems, the typical printed circuit board used in BCIs is often flat in shape and may fail to offer practical functioning in field conditions. Therefore, there is a need for a brain-computer interface with an improved form factor and adequate internal field computing resources.

BRIEF SUMMARY

Disclosed herein are embodiments of a brain-computer interface and headset, which includes an augmented reality display, one or more sensors, a processing module, at least one biofeedback device, and a battery.

In some embodiments, the interface may include a printed circuit board that contoured in a shape that conforms to a human head. The board may be a flexible board or may be a board with separate sections linked together. In an embodiment, the board comprises three parts: a first area, a second area and a third area. The first area of the printed circuit board may comprise the analog front end and may input brain-to-surface (of the skin) bio-signals using strategically located sensors. The second area of the printed circuit board may perform the processing, analyzing and mapping of bio-signals into an output, including haptic, audio, and visual outputs to the augmented reality glasses. The third area of the printed circuit board may provide haptic and audio feedback. After experiencing feedback from all, or any of these three sensory modalities—audio, visual and haptic, a user may generate new and different bio-signals from the brain, and as such a feedback loop may result in creating and strengthening neural pathways that lead to successful behaviors and actions by the user of the headset.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
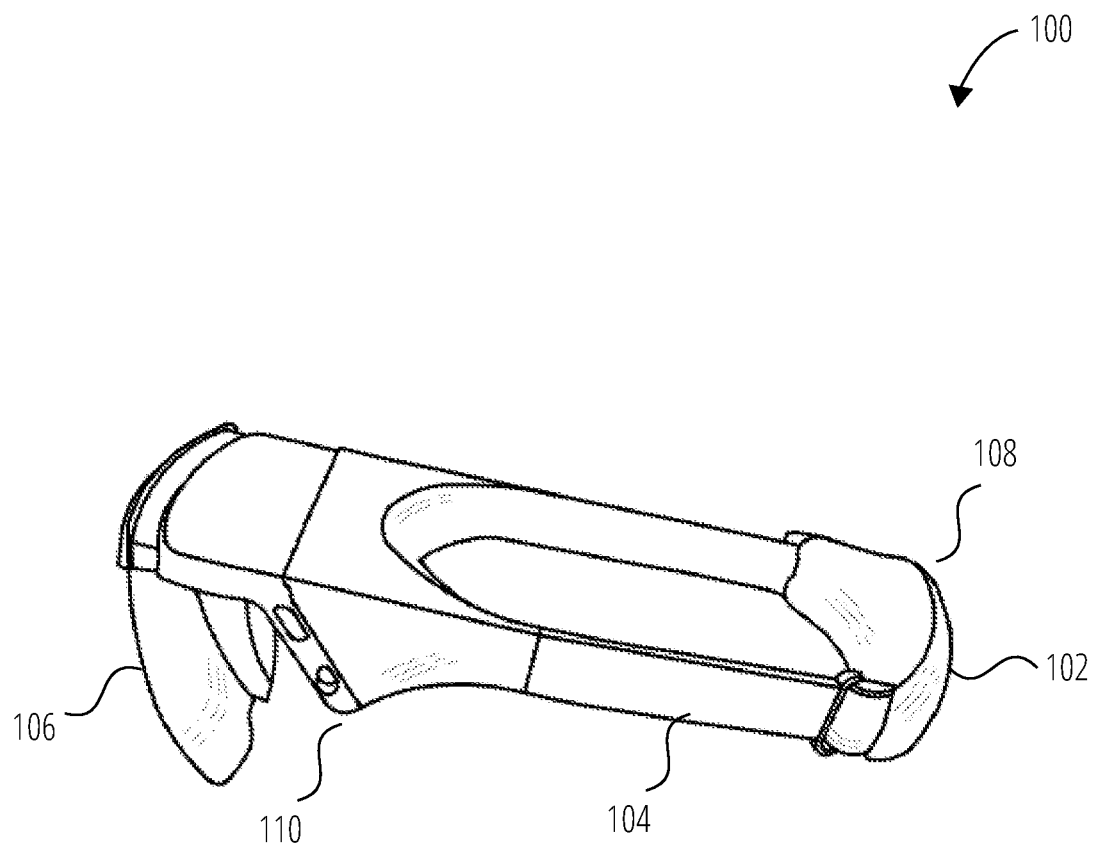
FIG. 1 illustrates a headset 100 in accordance with one embodiment.

The present disclosure addresses problems of comfort, wireless mobility, usability, reliability and other constraints found in conventional BCI systems utilizing a novel contoured shape and consolidated on-board processing of bio-signal data utilizing a specially-designed printed circuit board within the headset. This ability to internally process bio-signals may reduce or eliminate the need for an external mobile device or computer to do the bio-signals processing.

The bio-signal data is collected from the sensors on or connected to the headset, input into the printed circuit board on the headset, processed on the headset, and then output to transducers including but not limited to visual, auditory, and haptic transducers. In an embodiment, the circuit board may have a variety of sensors connected to the analog front end. For example, the mounted EEG electrodes may be utilized, but there may also be EMG sensors attached to an arm or other body part wired to the circuit board for processing data from multiple sources, not just EEG on the head.

The output may for example be applied to an augmented reality headset that a user may wear. The senses that may be stimulated as biofeedback may include, e.g. output commands sent to inflatable bags for pressure, temperature for increasing therapeutic sensation, electrical stimulation, or even a command to an external device or system such as a prosthetic hand/arm/leg or wheelchair for controlled movement.

In response to these outputs, new and altered neural signals of the user's brain may be reinforced, thus establishing a feedback loop that may result in discovering unique and creative ways to translate intentions into new experiences by the user of the headset.

The headset may function standalone without reliance on an external mobile device or computer, making it portable and self-sufficient as a "read-only" device, i.e., no ability to display augmented reality. Alternatively, it may communicate wirelessly with a mobile device or computer, providing output based on the bio-signals from the user of the headset. The headset is a unique design that consolidates more processing power into a smaller package than conventional BCI headsets. The portability factor may make a significant impact on individuals who want to have this experience in locations that are away from modern conveniences, as well as for people who are disabled. For example, one of the uses of this device may include an augmented assisted communications device or a remote control device. The systems and devices described in this disclosure may assist people who otherwise have a hard time communicating or enough physical ability to control their environment well. The brain signals of such people may be able to communicate their thoughts or remotely control objects in their environment, as opposed to verbal or hand-based communications.

Non-limiting examples of the configurations of the BCI or BCI+headset include:

BCI as a fully integrated system with AR

BCI as an accessory that can be bolted onto another AR/VR/Mixed Reality system

BCI as a reference design that can be miniaturized to a completely detached solution (e.g. BCI in a baseball cap and AR in a pair of smart glasses—worn separately but connected wirelessly)

BCI that can be miniaturized as an implantable under the skin and communicate wirelessly with a pair of smart AR contact lenses.

One embodiment comprises a fully self-contained EEG (electroencephalography) headset device that is specifically designed for the sensing and reporting of Visual Evoked Potential (VEP) matches, and optionally interfacing to a host computing device as a human Interface Device (HID) over Generic Attributes (GATT) device keyboards or mouse interfaces. In an embodiment, the Visual Evocation may be a steady state Visual Evoked Potential (SSVEP).

Evoked Potentials

Signals can be recorded from cerebral cortex, brain stem, spinal cord, peripheral nerves and muscles. Typically the term "evoked potential" is reserved for responses involving either recording from, or stimulation of, central nervous system structures. Evoked potentials are mainly classified by the type of stimulus: somatosensory, auditory, visual. But they could be also classified according to stimulus frequency, wave latencies, potential origin, location, and derivation.

Examples of VEPs that may be used with devices and systems disclosed herein include, but are not limited to:

Monocular pattern reversal
Sweep visual evoked potential
Binocular visual evoked potential
Chromatic visual evoked potential
Hemi-field visual evoked potential
Flash visual evoked potential
LED Goggle visual evoked potential
Motion visual evoked potential
Multifocal visual evoked potential
Multi-channel visual evoked potential - - -
Multi-frequency visual evoked potential
Stereo-elicited visual evoked potential
Steady state visually evoked potential
Code modulated visual evoked potentials
Chaotic code modulated evoked potentials
C1
P100
P200
P300
P600

Auditory evoked potentials (AEPs) are a subclass of event-related potentials (ERPs). ERPs are brain responses that are time-locked to some "event," such as a sensory stimulus, a mental event (such as recognition of a target stimulus), or the omission of a stimulus. For AEPs, the "event" is a sound. AEPs (and ERPs) are very small electrical voltage potentials originating from the brain recorded from the scalp in response to an auditory stimulus, such as different tones, speech sounds, etc. Examples of Auditory Evoked Potentials that may be used with devices and systems disclosed herein include, but are not limited to:

Brainstem auditory evoked potentials
C1
P100
P200
P300
P600

Somatosensory Evoked Potentials (SSEPs) are evoked potentials recorded from the brain or spinal cord when stimulating peripheral nerve repeatedly. Examples of SSEPs that may be used with devices and systems disclosed herein include, but are not limited to:

- Steady-state vibration (haptic) somatosensory evoked potentials
- Modulated Vibration (haptic) somatosensory evoked potentials
- Stereo-elicited vibration (haptic) evoked potentials
- Multi-frequency vibration (haptic) evoked
- C1
- P100
- P200
- P300

The self-contained device may comprise a headband or other external scalp sensor contact arrangement with one or more sensors. The device may also include support circuitry, such as a sensor amplifier, CPU, Analog to Digital (A2D) converter, and BLE (Bluetooth Low Energy) that interfaces with the HID over GATT protocol to a host. Acting as a HID wireless keyboard or mouse interface, this self-contained device may be used to control any HID interface compatible devices including but not limited to desktop computer, mobile devices and home appliances and media and entertainment equipment.

The device may be configurable for: (a) VEP matches on different frequencies that the device may monitor; (b) power threshold for the frequency; and (c) the number of consecutive repeated cycles over the threshold. The device may generate a configurable associated HID keyboard or mouse report to the HID Host. This capability may allow for direct control over iOS, Android, OSX, Windows, and Linux devices.

Artificial Intelligence (AI)

There are numerous machine learning methods that may be used to process biosignals. Examples include, but are not limited to:

- PSDA—Power Spectral Density Analysis
- CCA—Canonical Correlation
- CNN—Convolutional Neural Network
- DNN—Deep Neural Network
- RNN—Recurrent Neural Network Multithreaded processing for simultaneous processing of data from multiple sources concurrently may be used. For example, Machine Learning for processing EEG (brain) and EMG (arm) simultaneously requires time synchronization between the two data streams and processing of EEG and EMG independently, but also processing the data as a combined set (i.e., sensor fusion). The disclosed systems and apparatuses make it possible to support sensor fusion onboard and wirelessly. Examples may include fusing streaming data from another sensor with the EEG sensors to decrease the uncertainty level of the output; and processing either the raw data, the features, or the combined 'simmer' data.

The systems and methods may support concurrent processing of biosignal data from multiple data sources and sensors (EEG, EMG, EOG, EYE TRACKING, MOTION, ECG), which requires a machine learning approach for efficient and rapid processing of big data on constrained devices.

On the communication application side (Speech Generating Application that runs on the AR portion of the headset), there is other AI running specifically for the Natural Language Processing, Natural Language Understanding aspects. Various embodiments of the system may utilize: Syntactic prediction models—Linear Word or Phrase prediction based on tree structured logic so that it makes grammatical sense in a chosen language (e.g. Spanish syntax is different than Portuguese syntax); Semantic prediction models—Non-linear Word or Phrase predition based on graph data from other sources and multiple meanings of a word or phrase (the same word or phrase can mean different things with the same language); and Combined Syntactic/Semantic models—Ability to graph complex meaning associated with words or phrases and assemble or compose an expression in a non-linear way such that the "meaning" of the expression is understood and contextually relevant.

Embodiments of the system may provide user configurable graphical interfaces that allows them to choose between a variety of keyboard configurations including radial word prediction for rapid sentence composition, traditional QWERTY and alphabetical keyboards, clustered linotype keyboards, word and phrase prediction, save words and phrases for future use in predictive models.

Embodiments of the system may use at least one sensor or meta-data source to automatically configure or allow a user to manually configure respective predicted words to be more context aware and semantically relevant and understandable. This may result in language that may be composed non-linearly. For example, a syntactical predictive model attempts to get the next word based on the previous word or words, upon a set of syntactical rules. However, with context awareness and semantic processing, one can predict a phrase with a set of letters or words that would normally be later in the phrase. For example, typing "Fish" in a syntactical only system may predict several words after "Fish" such as "Swim", "Are", "Can", "Eat" which may not be relevant to the user requiring more effort to continue typing to get the words they want to say. By integrating sensors to inform a semantic understanding, such as chronofencing with real-time clock and geofensing with GPS and/or wi-fi connection identification, at typical dinner time, a user could type "Fish" and the semantic+syntactical predictive model could suggestion "I'd like to eat Fish and chips" based on sensor data and language customization and favorites.

Meta-data sources may include, but are not limited to:

- Magnetic/Mechanical Sensors: Compass; Magnetometer; Strain sensors; Search-coil magnetometer; Fluxgate magnetometer; Superconductor magnetometer; Hall effect sensor; Magnetoresistive magnetometers; Spin-vale transistors; Giant magnetoimpedance magnetic sensors; Magnetodiode; Magnetotransistor; Magnetostrictive magnetometers; Magneto-optical sensor; MEMS Based Magnetometers; Ball/tilt/foot switch; Sole pressure switch; Pressure sensors; Contact sensors; Mechanical switches
- Environmental Sensors: Barometer; Humidity; Light sensor; Thermal sensor; Ambient air temperature and pressure; Photometer
- Location sensors: GPS receiver; Automatic Vehicle Identification (AVI) readers; Real-Time Location Systems (RTLS); Wi-Fi Location-Based Services; Satellite systems
- Temporal sensors: Real-Time clock; Calendar; Seasonal data
- Motion sensors: Accelerometer; Gyroscope; Pressure sensor; Gravity sensor; Inclinometer; Pedometer; Rotation sensor; Speedometer; Rotational vector sensor; Orientation sensor; Radar sensors
- Imaging/Video sensors: Digital camera; 3D camera; Optical sensor; Infrared sensor; Ultrasound sensor; Lidar sensor
- Proximity sensors: Proximity sensor; Touch sensor; RFID; Tactile sensor; NFC Acoustic sensors: Microphone; Silicon microphones; Acoustic wave devices; Surface acoustic wave, Sonar Medical/Biometric sensors: EEG; ECG; EMG; EOG; EDA; Photoplethysmogram; Blood pressure and arterial tonometry; Respiration; Dosage control/detection; Stress sensors; Heart rate sensors; electrooculography (EOG); electrodermal activity sensors; ECOG sensors; vascular implant sensors; Retinal implant sensors; Corneal implant sensors; Wearable optical sensors such as contact lenses, glasses or visors; In-ear acoustical sensors; Cochlear implant sensors Chemical sensors: Oxygen saturation; Aroma sensors; Metal-oxide; Semi conductive polymers; Conductive electro active polymers; Electrochemical gas sensors; Actinometer Optical sensors: Photoplethysmography sensors; Fiber optic sensors; Infrared sensors; Radio Frequency (RF) sensors; Ultraviolet sensors Force sensors: Force sensitive resistor; Mass sensors: Fingerprint sensors; Air pressure sensors Photoelectric sensors: Oximeter Any of the sensors above may be part of the system, or external to the system. If external to the system, the system may have wired or wireless connection to the external sensors. If wireless, this connection may be directly via a dedicated wireless network connection, or via an open or semi-secure wireless network.

The BCI may utilize AI for pattern-recognition and personalization. Traditional BCI+AI solutions are limited to fixed locations, expensive equipment, and ultra-high-speed continuous Internet connections.

The BCI may utilize an "Offline-First" design approach. The Offline-First techniques optimize and personalize the BCI performance even when offline.

When online, Machine Learning (ML) training is applied to create an individualized Recognizer-Categorizer (RC). Derived outputs of the ML training are stored into an Expert system (ES) knowledgebase in the cloud.

The ML & ES are not used in a conventional real-time system. The Synthesized Insights (SIs) derived from the ML & ES are used in a novel way to generate individualized executable Recognizer-Categorizers that may be automatically loaded into the BCI device (e.g., storage of the printed circuit board) for offline usage.

The present disclosure is directed to methods including AI utilized in the cloud to enhance resource constrained IoT. The apparatuses in the disclosure include wearable and implantable devices that run individualized code locally generated by AI where a continuous, ultra-broadband streaming connection to the cloud is not reliable.

This disclosure provides solutions to adding AI to mobile device that cannot support AI locally or in a mobile context. In addition to processing brainwave data utilizing AI, the methods and systems developed for this BCI+AI may also be generally applicable to a wide-range of resource-constrained IoT, wearable and implantable devices.

In embodiments of a BCI headset, several AI techniques may be utilized. ML may be utilized as an auto-tuning dynamic noise reducer, a feature extractor, and a Recognizer-Categorizer. It is also a pipeline of training data input into the ES knowledgebase. The ES evaluates recognized brainwave patterns that are leveraged into the offline RCs. The ES has the knowledge to create personalized and AI optimized RCs that may operate locally on Resource Constrained Devices (RCDs). An RCD may be a device that has limited processing and storage capabilities, and that often runs on batteries. This may offer a superior robustness and functionality for BCI that conventional techniques would not. Offline ML training feedback is incorporated by storing EEG EPOCs of successful recognition matches for re-integration into training sets synchronized upon the next online session.

The BCI headset may be a battery-powered, wireless, consumer-grade bio-signal sensing device comprising a two-sensor, three-contact point (2 sensors, ground-reference), a processor, and BLE (Bluetooth Low Energy) connectivity, specifically designed for the detection and processing of SSVEP brain signals to act as a BCI by monitoring cranial points ($O_1$-$O_2$).

The present disclosure is directed to a brain computer interface in a headset that may correlate the printed circuit board (PCB) with brain waves and other bio-signal sources that are being processed. The PCB may utilize a microcontroller that includes a Bluetooth low energy module, a microprocessor, and a USB bridge. Further, in an embodiment, the EEG Analog-to-Digital processor includes an analog front end that receives channels using Texas Instruments ADS1299, which sends out signals through a serial peripheral interface (SPI) buffer to a microprocessor. The brain waves may be recorded using a micro SD. Additionally, the user may download music, sounds, or any haptic sequences, into the micro SD. In an embodiment, the headset may include a motor amplifier OLED module, which may be a 2 line by 180-pixel OLED such as an I2C OLED. From a visual perspective, the OLED module provides a feedback mechanism that may allow the user to view and or modify onboard BCI settings.

The haptic Motor Controller may include a built-in microcontroller chip that includes fundamental haptic vibrations. The user may stack those vibrations and may also create vibrations based on audio, or setup the haptic vibrations to make the headset vibrate to the music.

Audio feedback may include various fundamental tones. In an embodiment, the user may Add, Modify, or Manage audio feedback on the brain computer interface.

Operating Modes

Four modes of operation of the BCI headset may include: Raw, Simmer, Cooked, and human interface device—keyboard (HID-KB).

Raw Mode:

The raw mode may stream the full bio-signal sensor data stream, which may include an EEG sensor stream, for further processing locally or in the cloud via a mobile or desktop internet connected device which may filter, recognize, or interact with the data. This mode is useful for training an AI and/or cloud-based recognition system.

Simmer Mode:

The simmer mode is a hybrid combination between the Raw and Cooked modes. The on-board processor may intersperse the raw data stream with custom (Cooked) messages. This mode is most useful when training an AI and/or cloud-based recognition system and comparing it to the local recognizer and diagnoses.

Cooked Mode:

The cooked mode is a fully processed custom message that may be generated by the local recognizer and diagnoses. No Raw data is passed. This reduces the bandwidth needed for operation.

HID-KB Mode:

The HID-KB mode configures the headset interface to appear to be a standard Bluetooth keyboard. This allows the headset to work with many applications including but not limited to desktop computer, mobile devices and home appliances and media and entertainment equipment. One advantage of HID-KB mode is to allow SSVEP to be used with the operating system accessibility features. It also may allow the headset the universal access to be utilized with many computers and operating systems that can utilize a Bluetooth keyboard. In an embodiment, the printed circuit board can emulate a Bluetooth keyboard and output to a mobile device, a computer, a car windshield, a plane windshield, a motorcycle visor, a motorcycle helmet, virtual reality glasses, mixed reality glasses, or the augmented reality glasses at least one of: a letter; a character; a number, and combinations thereof.

Device Construction

The two main sensors may be moved to the center or front of the user's head, the headset may efficiently detect and track various brain waves, such as beta waves or theta waves. The headset's implementation is not limited to two sensors but has the ability to have up to eight sensors, a ground, and a reference.

The headset and printed circuit board are sensitive to visually evoked potentials, audio evoked potentials, and motion evoked potentials. They are also sensitive to steady state visually evoked potentials in the AR headset, which includes a blinking light.

In one embodiment of the printed circuit board, the printed circuit board is limited in functionality to visually evoked potentials, which allows for even faster processing entirely on the printed circuit board, and without the use of the cloud or an external computer.

In another embodiment of the printed circuit board, the printed circuit board is limited in functionality to audio evoked potentials, which allows for even faster processing entirely on the printed circuit board, and without the use of the cloud or an external computer.

In another embodiment of the printed circuit board, the printed circuit board is limited in functionality to haptic evoked potentials, which allows for even faster processing entirely on the printed circuit board, and without the use of the cloud or an external computer.

The printed circuit board may be preconfigured to map certain inputs from EEG (Electroencephalography), ECG (Electrocardiography), EMG (Electromyography), EOG (ElectroOculography), functional near-infrared spectroscopy (fNIRS), ECG, EEG, or other bio-signals, to particular types of feedback. The printed circuit board is configurable in terms of sound, music, words, visuals that are projected, and haptic files. The printed circuit board also has defaults of sound files, haptic files, certain algorithms for feature extraction, and pattern matching.

For example, the headset can be preconfigured to output the letter "A" when the printed circuit board reads the signal 10 hertz. Similarly, all alphabet, numbers, words, music and haptic vibrations may be mapped to an audio, visual or haptic input.

Furthermore, such pre-configurations can be customized to each user, such that there may exist customized vibration files, sound files, or different algorithms that are specific to a customer or user. These pre-configurations may be implemented wirelessly from an application, so the user does not have to plug into the USB of the printed circuit board.

For example, given three frequencies, 7, 11, and 19 hertz, accessibility controls may be set to move to previous item, next item, or select item respectively. For example, if the printed circuit board reads the signal 7 hertz, then the "previous item" control may pop up on the AR headset.

In an embodiment, each user may have a dedicated 'private cloud' with all of their own data, personalized files and preferences, allowing the BCI to synchronize with the server when it connects to the internet.

In an embodiment, Over the Air downloads or firmware updates may be pushed to the BCI. The updates may be event-based changes or full system updates.

The connection used to attach the printed circuit board to the augmented reality glasses may be severed, thus enabling the printed circuit board to be connected to another pair of augmented reality glasses while maintaining all the functionality of the printed circuit board. The headset is capable of functioning with different augmented reality glasses, such as Microsoft Hololens™, Magic Leap™, and other products that can provide augmented reality through a visual display for a human being.

In an embodiment, a system of a brain computer interface in a headset includes: an augmented reality display; one or more sensors for reading a bio-signal from a user; a processing module, including a processor that analyzes the bio-signal and maps the bio-signal into an output for a digital interaction device, wherein the digital interaction device includes at least one of the augmented reality display, a digital interaction device in close proximity to the user, a remotely located digital interaction device, and combinations thereof; at least one biofeedback device in communication with the processing module, wherein the at least one biofeedback device is configured to provide feedback to at least one of the user, the digital interaction device, and combinations thereof; and a battery, wherein the battery provides power to at least one of the augmented reality display, the one or more sensors, the processing module, the at least one biofeedback device, and combinations thereof.

In an embodiment, a method of implementing a brain computer interface (BCI) in a headset includes utilizing an augmented reality display; utilizing one or more sensors for reading a bio-signal from a user; utilizing a processing module, including a processor that analyzes the bio-signal and maps the bio-signal into an output for a digital interaction device, wherein the digital interaction device includes at least one of the augmented reality display, a digital interaction device in close proximity to the user, a remotely located digital interaction device, and combinations thereof; utilizing at least one biofeedback device in communication with the processing module, wherein the at least one biofeedback device is configured to provide feedback to at least one of the user, the digital interaction device, and combinations thereof; and utilizing a battery, wherein the battery provides power to at least one of the augmented reality display, the one or more sensors, the processing module, the at least one biofeedback device, and combinations thereof.

The headset addresses the difficult commercial problem of resource constraints in BCI headsets, while improving functionality over conventional designs. The headset may also liberate users with full mobility, which makes it possible for researchers to perform true longitudinal studies in the field, as well as end users greater freedom to explore and interact with their environment.

The bio-signals are processed and analyzed in real-time. By doing more processing on the printed circuit board, costs are reduced by eliminating additional electronic equipment and reducing the amount of costly time and effort to setup and use it, thereby enabling more frequent use.

Furthermore, the latency of feedback responses is reduced through the augmented reality, haptic, and/or audio systems.

Referring now to the drawings, FIG. 1 illustrates an embodiment of a headset 100 that comprises a PCB 102, a strap 104, a display 106, a contoured sleeve 108, and a visual display source 110. The display 106 and visual display source 110 may be any AR headset, and is not limited thereto. The PCB 102 is curved in shape to contour around the back of a human head. The contoured sleeve 108 secures the PCB 102 and other items such as batteries. The strap 104 may circumvent the PCB 102 and around the back of the human head and maintain the headset 100 in contact with the back of the human head. In some embodiments, the strap 104 traverses the contoured sleeve 108; however, the strap 104 may also traverse the outside rear surface of the contoured sleeve 108 or may be manufactured as a part of the contoured sleeve 108. The strap 104 may couple the PCB 102 electrically and physically to the display 106 and the visual display source 110. The PCB 102 may output a video signal to a user through the visual display source 110 and display 106. In some embodiments, the display 106 provides augmented reality images. The headset 100 is an exemplary example of a headset useful for the systems and methods of this disclosure, and is not limited to the components shown in FIG. 1 or FIG. 2.

Figure 2:
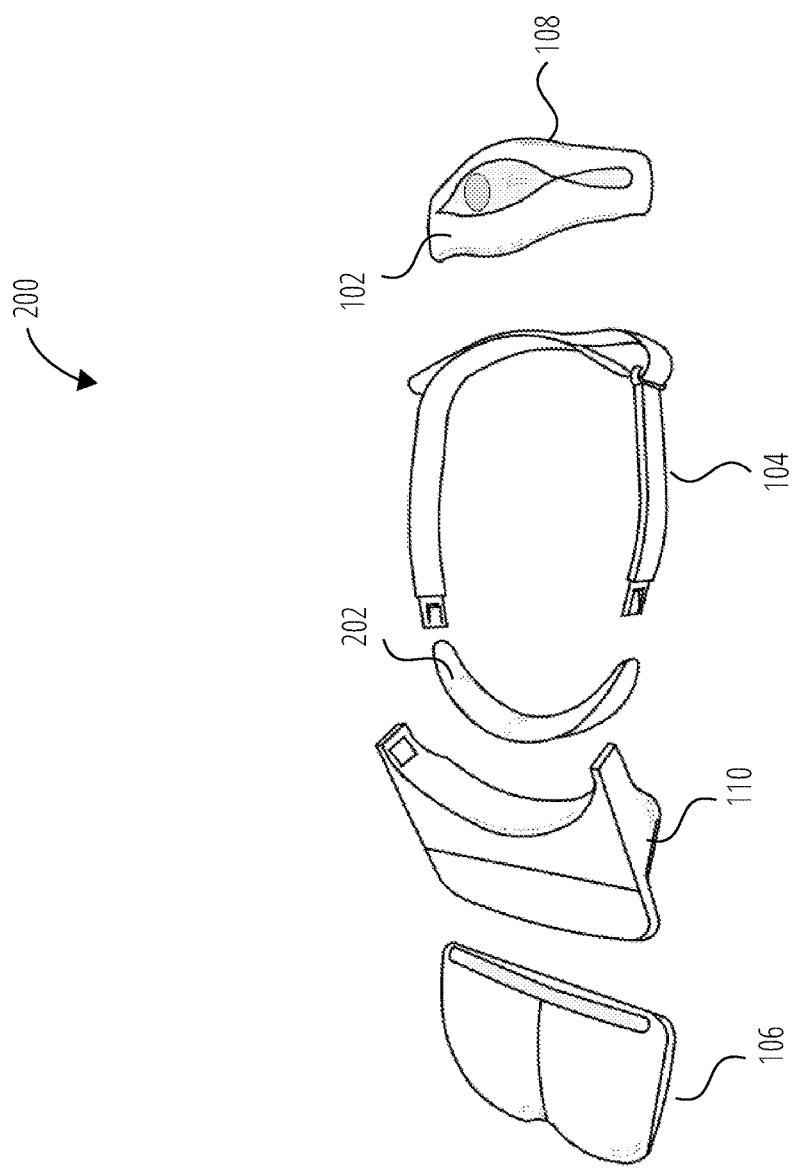
FIG. 2 illustrates a disassembled BCI headset 200 in accordance with one embodiment.

In FIG. 2, the disassembled BCI headset 200 comprises a PCB 102, a strap 104, a display 106, a contoured sleeve 108, a visual display source 110, and a pad 202. The pad 202 may be located on the visual display source 110 and provides a cushion between a user's forehead and the portion of the visual display source 110 in contact with the user's forehead. The disassembled BCI headset 200 is an exemplary example of a headset useful for the systems and methods of this disclosure, and is not limited to the components shown in FIG. 2.

Figure 3:
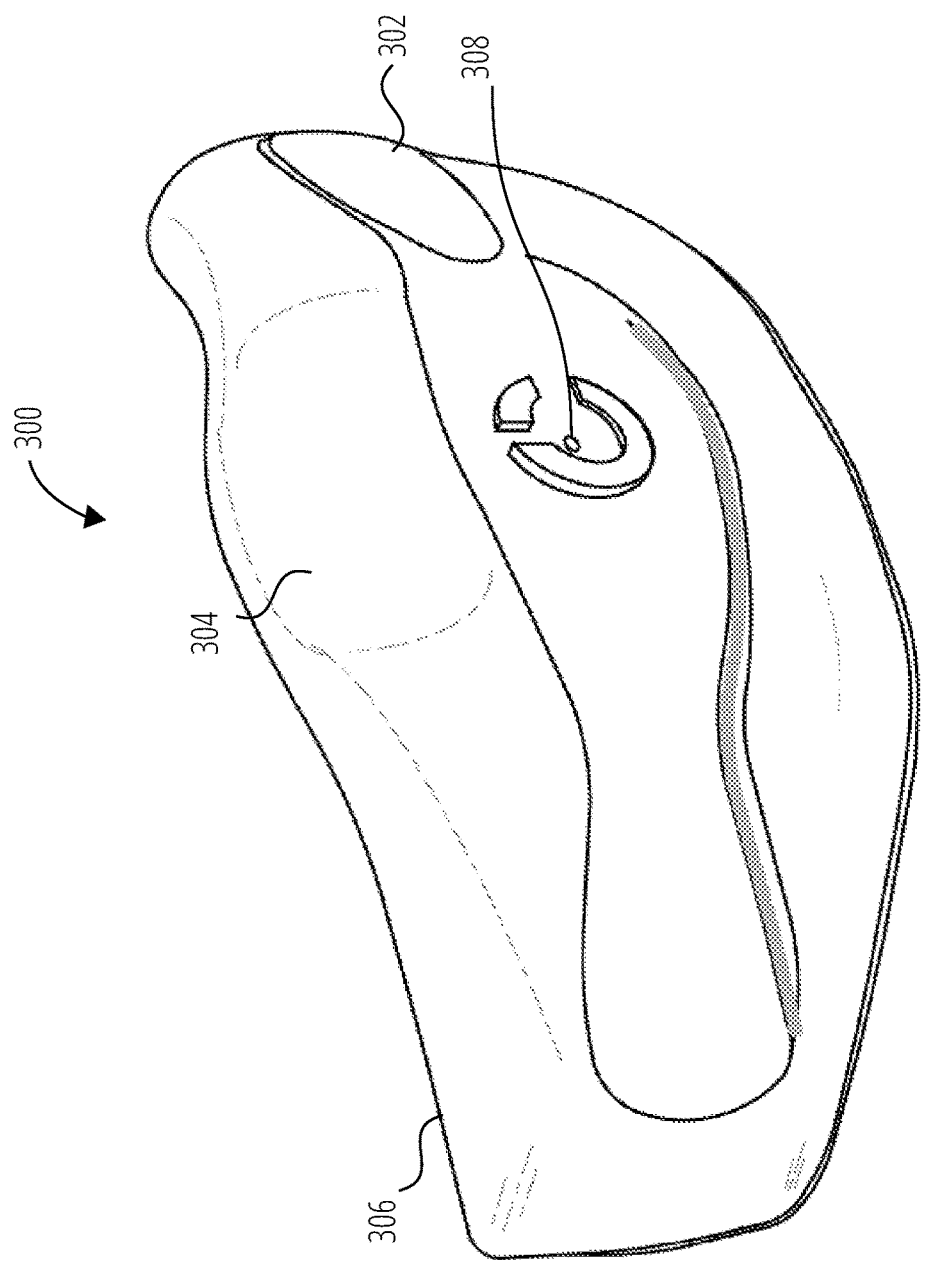
FIG. 3 illustrates a headset 300 in accordance with one embodiment.

FIG. 3 shows a front oblique view of headset 300 comprising a contoured sleeve 306, a cover 302, a led 308, and a PCB 304. The contoured sleeve 306 may include a PCB 304. The first area of the PCB 304 may include an analog front end and allows the headset 300 to read EEG (Electroencephalography), ECG (Electrocardiography), EMG (Electromyography), or other bio-signals. The cover 302 provides access to the PCB through the contoured sleeve 306.

In an embodiment, there is a hole (led 308) in the contoured sleeve 306 that allows a multicolor LED light to be piped out and visible externally to provide a user with color coded status indications such as power on/off, flickering, if there is data/activity, color coded for different modes, etc. The led 308 may be in the center of the contoured sleeve 306 but is not limited thereto. In an embodiment, this functional lighting indicator may be a single led light, multiple led lights, animated lights, etc. The light indicator functionality may be personalized for the individual user.

Figure 4:
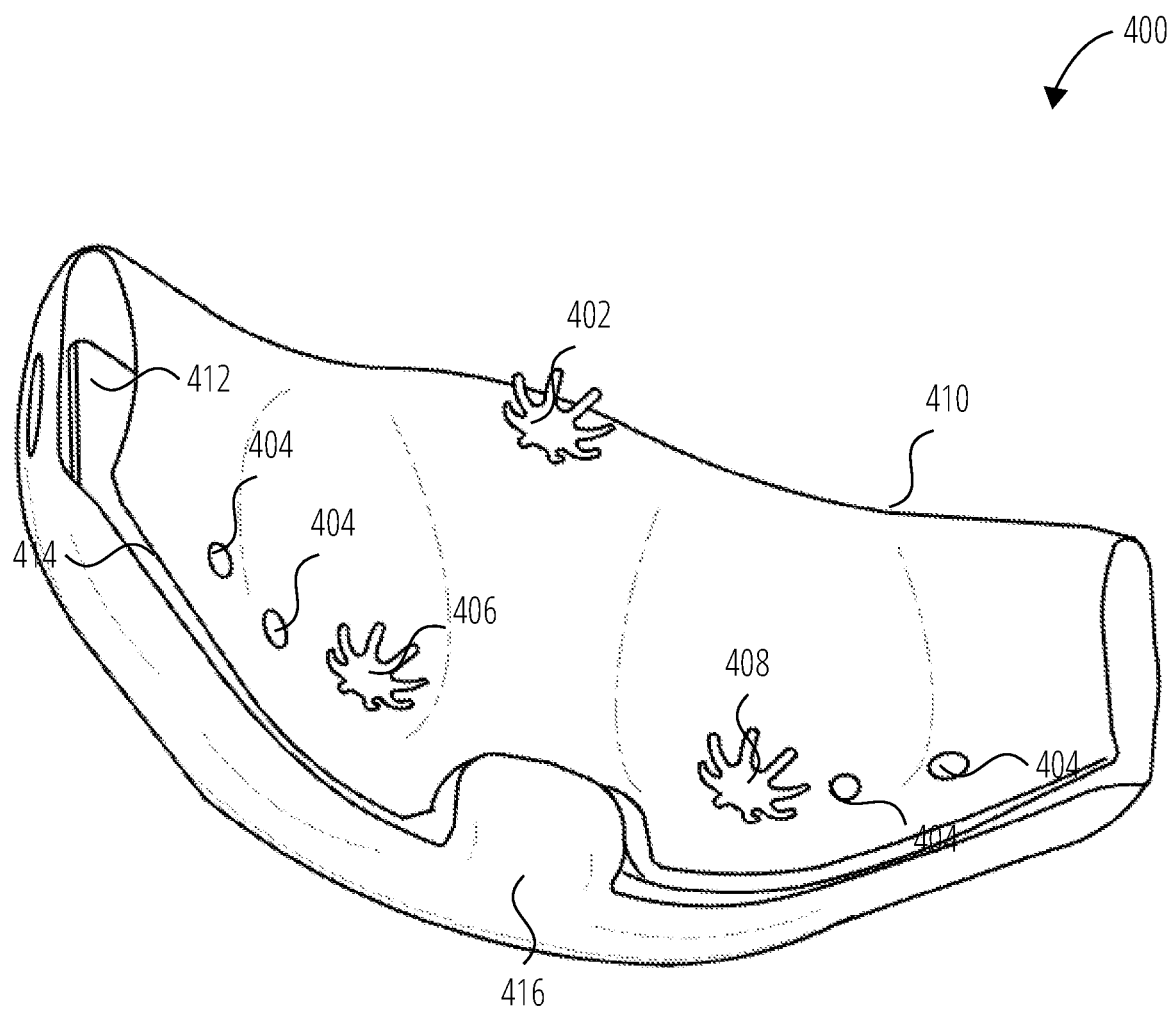
FIG. 4 illustrates a headset 400 in accordance with one embodiment.

Referring to FIG. 4, a portion of a headset 400 comprises a contoured sleeve 410, a sensor 402, a sensor 406, a sensor 408, additional sensors 404, a PCB 412, a slit 414, and a clasp 416. The contoured sleeve 410 may include three sunburst-type shapes on the portion of the headset that are formed to contact the human's head, the shapes representing sensor 402, sensor 406 and sensor 408. The shapes representing the sensors may be any shape. In an embodiment, the shape is recessed into the contoured sleeve 410. The recessed area enables the sensors to be more comfortable and stable. In some embodiments, the sensors may be adjusted up, down, left, or right. The sensor 402, sensor 406 and sensor 408 detect brain signals, and apply them to the PCB 412, where the PCB 412 processes brain signals. There are 4 additional sensors 404. These additional sensors may also sense brain signals and apply them to the PCB 412 for further processing.

In another embodiment of the headset 400, the headset has four additional sensors 404, instead of seven total sensors.

Different embodiments of the PCB 412 may utilize cables between break points in the printed circuit board, such that the layout of sensors can be six 1×1s or three 2×1s, or three 1×2s.

The contoured sleeve 410 may include a slit 414 between the rear surface and the bottom surface. The slit 414 may be opened by releasing the clasp 416 and spreading apart the bottom and rear of the contoured sleeve 410. This slit 414 may serve to allow exchangeability of different kinds of head straps.

Figure 5:
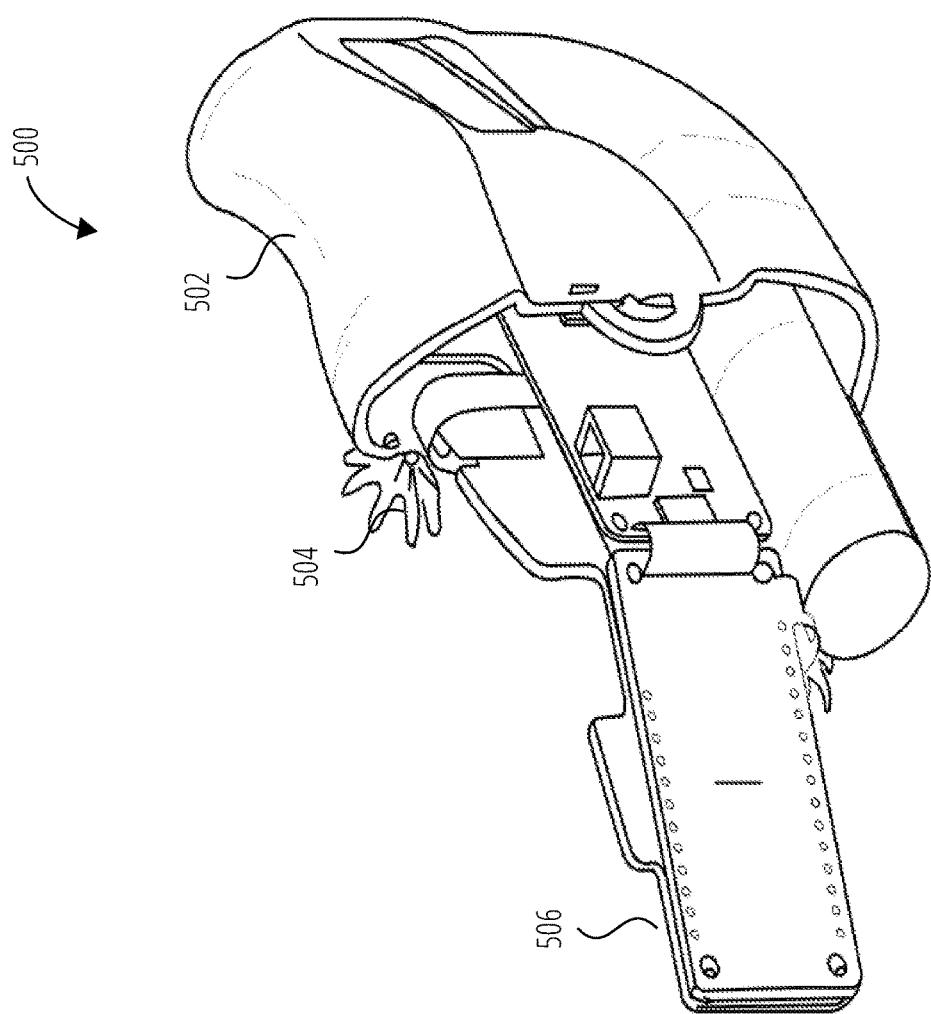
FIG. 5 illustrates a cross section of headset 500 in accordance with one embodiment.

Referring to FIG. 5, a cross section of headset 500 according to an embodiment includes a contoured sleeve 502, a third area 506 of the printed circuit board, and a sensor 504 attached to the contoured sleeve 502 of the headset. Although three areas are shown, the printed circuit board may be a single flexible board where the positioning of the components on the board is not critical.

The third area 506 provides haptic feedback. The bio-signals may be processed and analyzed in real-time. The bio-signals are processed locally in the headset 400 and therefore are not streamed online or in the cloud. This is referred to as localization.

Figure 6:
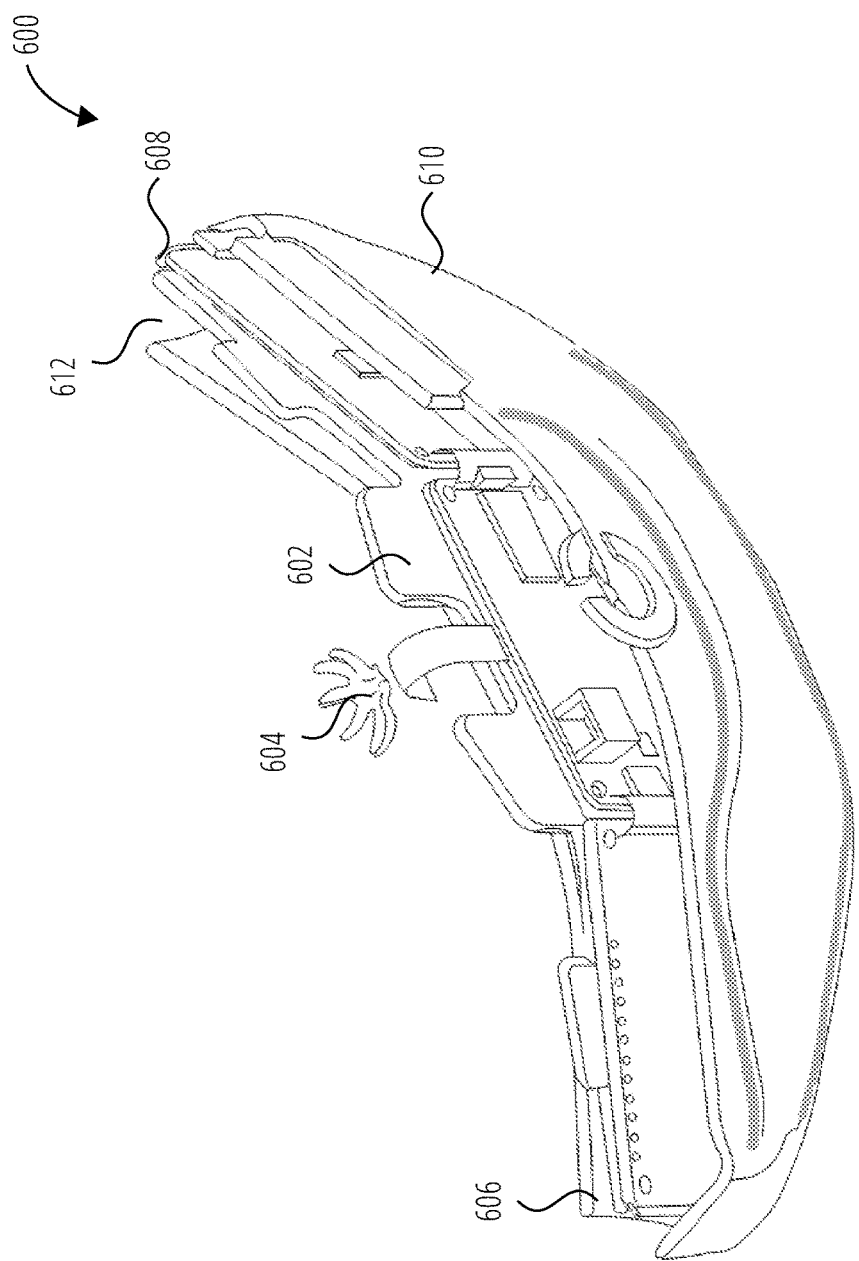
FIG. 6 illustrates a cross section of headset 600 in accordance with one embodiment.

Referring to FIG. 6, a cross section of headset 600 according to one embodiment includes a contoured sleeve 610, a first area 608, a second area 602, a third area 606, and a sensor 604. The top of the contoured sleeve 610 has been removed to show the embedded printed circuit board in the headset. A sensor 604 is attached to the third area 606 of the printed circuit board. The cross section of headset 600 also shows the first area 608 and the second area 602 of the printed circuit board. In an embodiment, there is a channel 612 area where an AR headset strap may pass through the inside of the BCI. The channel 612 may be present from one side of the BCI to the other (near the third area 606). In an embodiment, there is a hole on either side of the BCI where both ends of the AR headset strap may come through.

Figure 7:
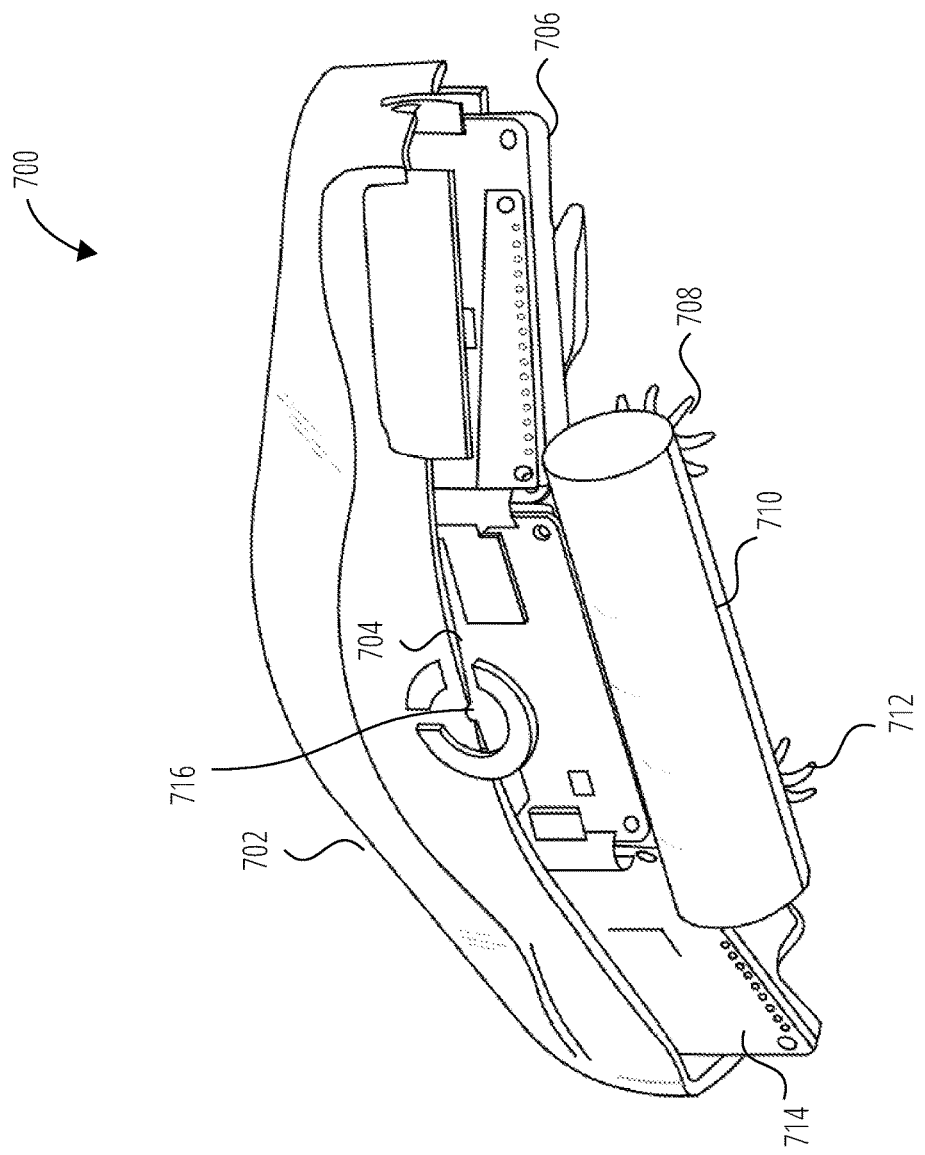
FIG. 7 illustrates a cross section view of headset 700 in accordance with one embodiment.

Referring to FIG. 7, a cross section view of headset 700 comprises a contoured sleeve 702, a first area 706, a second area 704, a third area 714, a battery 710, a sensor 708, and a sensor 712. The battery 710 may be a LiPo, LiOn, etc., battery and may be a custom shape/designed battery.

The cross-section view of headset 600 with the bottom of the case removed shows a PCB inside of contoured sleeve 702 and demonstrates how the PCB is embedded into the headset. The first area 706, the second area 704 and the third area 714 are shown on the PCB. A battery 710 is located in the bottom portion of the headset. There is a sensor 708 and a sensor 712 attached to the battery 710. The headset 600 may also have a status led 716.

Figure 8:
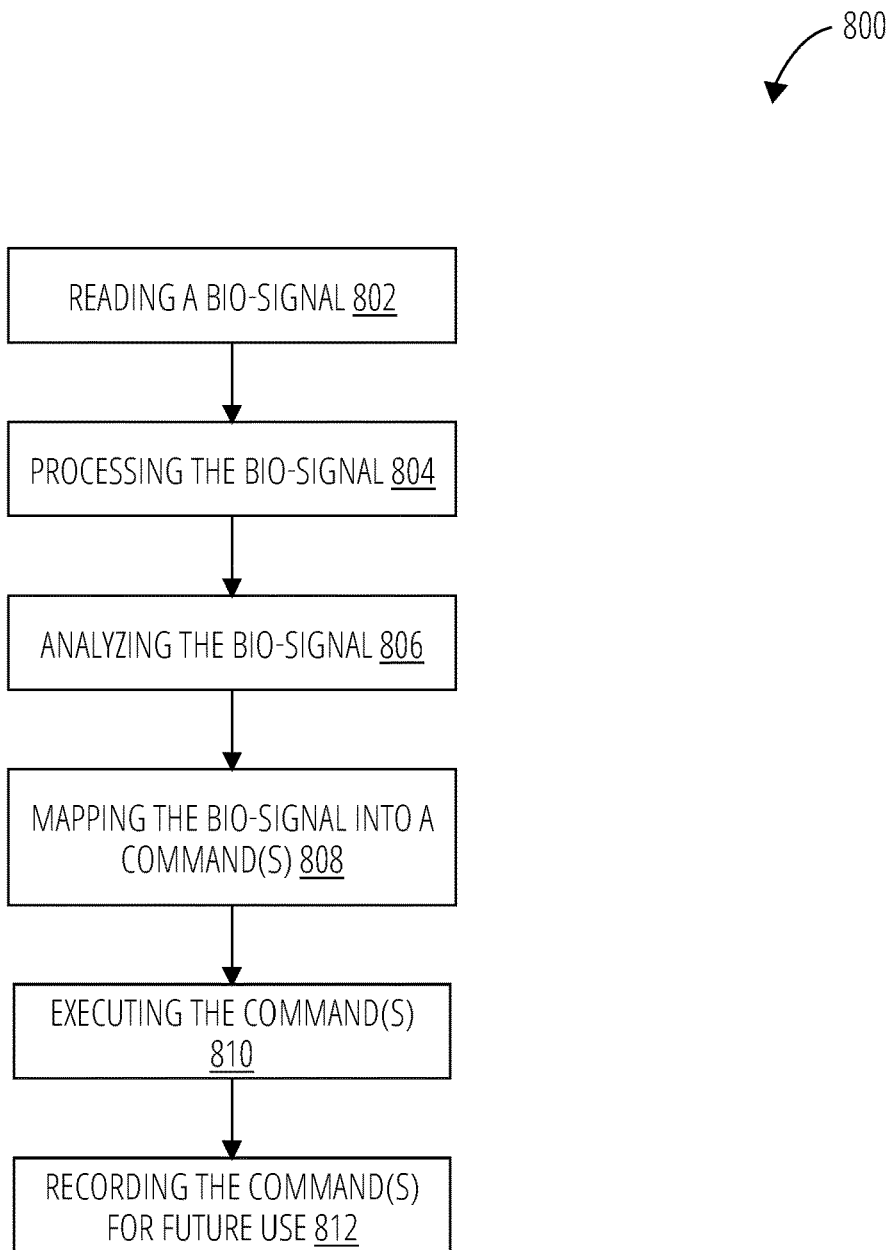
FIG. 8 illustrates a method 800 in accordance with one embodiment.

Referring to FIG. 8, a method 800 includes the steps involved to implement a brain computer interface in a headset. The steps include reading a bio-signal using the first area of the PCB as an analog front end (block 802), processing the captured bio-signal (block 804), analyzing the bio-signal (block 806), mapping the bio-signal into command(s) (block 808), executing the command(s) (block 810), and recording the command(s) for future use (block 812).

The method 800 may be a closed loop method for reading brainwaves via the BCI and writing to the brain via bio-feedback through the user's somatosensory system (sight, sound, vibrations/haptics). In an embodiment, the closed loop system reads the visual cortex via the occipital lobe (visual) and writes to the somatosensory cortex (senses).

In an embodiment, the processor analyzes the bio-signal and maps the bio-signal into an output for a digital interaction device. The digital interaction device may include at least one of the augmented reality display, a digital interaction device in close proximity to the user, a remotely located digital interaction device, and combinations thereof. Digital interaction devices in close proximity to the user may include a smart phone, a tablet, a computer, etc. Remotely located digital interaction devices may include remotely located computers, tablets, smart phones, monitors, etc.

In an embodiment, the commend is at least one of the following: do nothing; log the data for later use; play an audio file; manipulate a visual element; play a vibration pattern; send a message or command to another device; remotely control a prosthetic limb; turn on/off the lights; change a tv channel, and combinations thereof.

In an embodiment, the commands may be recorded for future use and improved machine learning performance as well as human neural performance/recall as reinforcement learning.

In an embodiment, the bio-signal that the PCB can read includes at least one of EEG (Electroencephalography), ECG (Electrocardiography), EMG (Electromyography), EOG (Electroocculography), visually evoked potentials, steady state visually evoked potentials, steady state audio evoked potentials, and motion evoked potentials.

Figure 9:
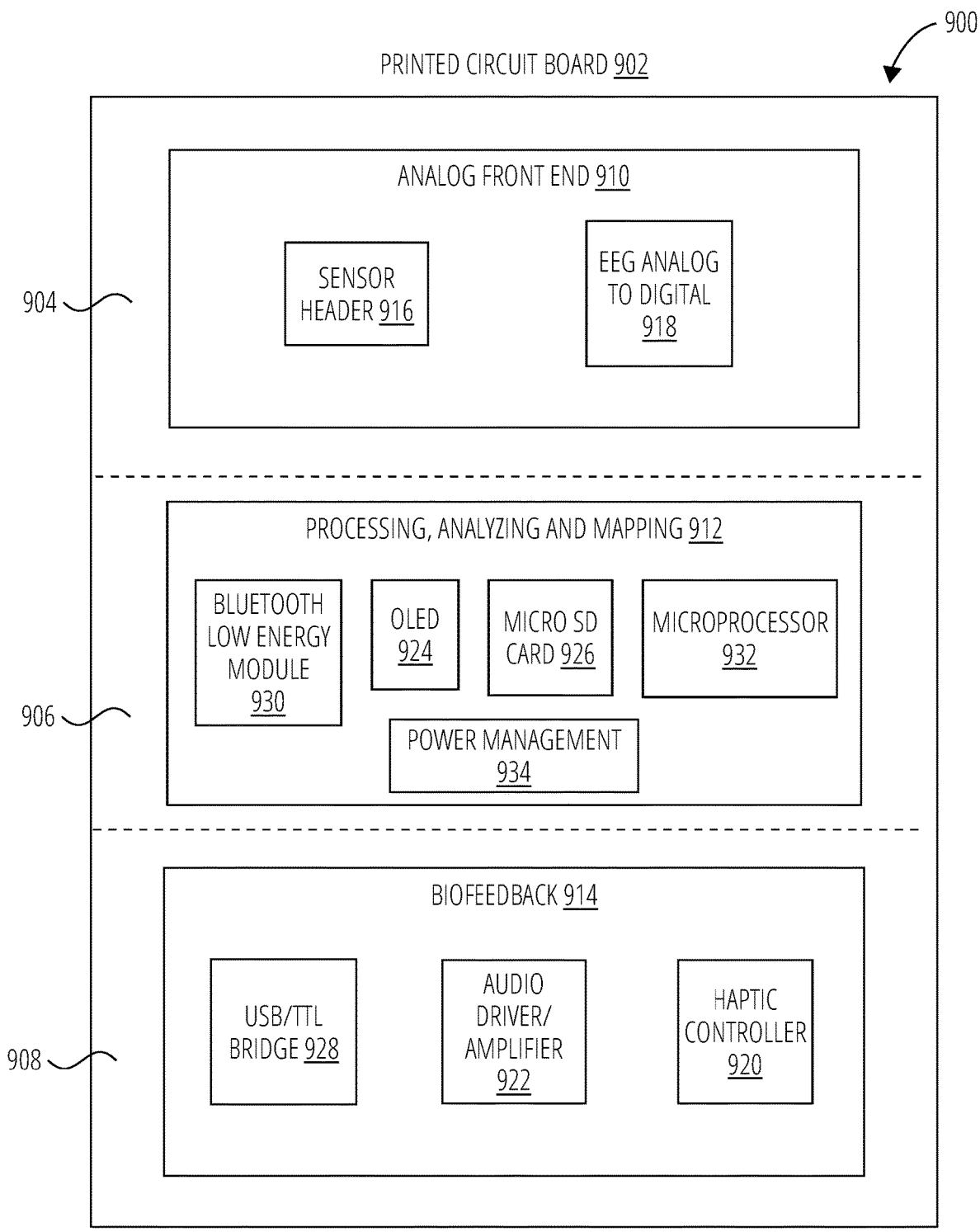
FIG. 9 illustrates a device 900 in accordance with one embodiment.

Referring to FIG. 9, a device 900 comprises a printed circuit board 902, a first area 904, a second area 906, a third area 908, an analog front end 910, processing, analyzing and mapping 912 logic, a biofeedback 914, a sensor header 916, an EEG analog to digital 918, a haptic controller 920, an audio driver/amplifier 922, an OLED 924, a micro sd card 926, a USB/TTL bridge 928, a Bluetooth low energy module 930, a microprocessor 932, and power management module 934.

The printed circuit board 902 comprises three areas, the first area 904 (analog front end 910), the second area 906 (processing, analyzing and mapping 912) and the third area 908 (biofeedback 914).

The first area 904 is the analog front end 910 that includes sensor header 916, EEG analog to digital 918 converter and the like. The first area of the printed circuit board receives the bio-signal and converts it to a digital signal. The second area 906 includes Bluetooth low energy module 930, OLED 924, micro sd card 926, microprocessor 932, power management module 934, and the like. The second area of the printed circuit board processes and analyzes the bio-signal using the microprocessor 932 and maps the bio-signal into an output on the augmented reality glasses. The output may include audio and visual output or a haptic output. The power management module may control power to the various components and modules, including the Bluetooth low energy module 930. The third area 908 provides a biofeedback 914 using a USB/TTL bridge 928, an audio driver/amplifier 922, or a haptic controller 920.

Figure 10:
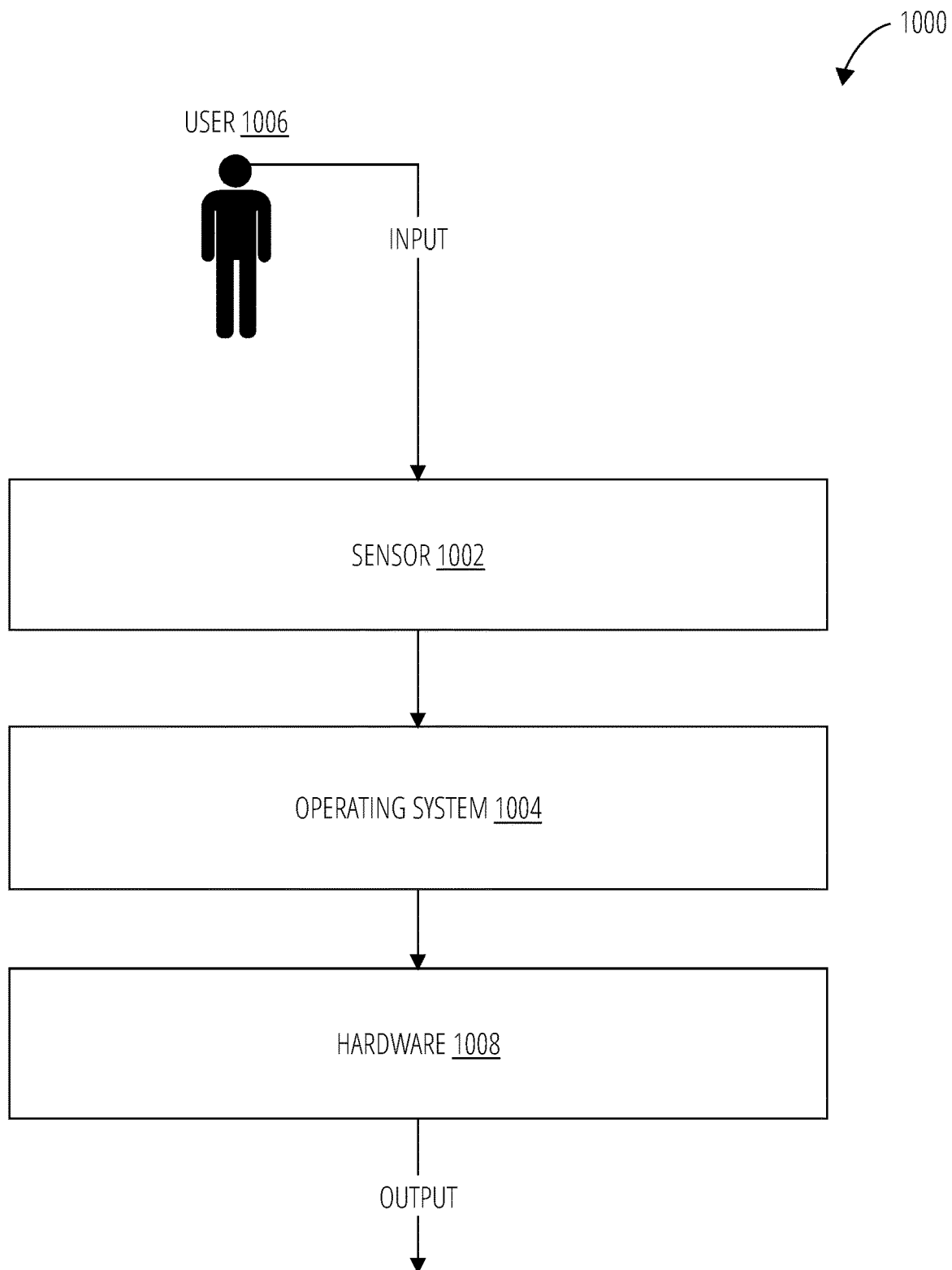
FIG. 10 illustrates a BCI+AR system 1000 in accordance with one embodiment.

FIG. 10 illustrates a BCI+AR system 1000 in accordance with one embodiment of the disclosure. A sensor 1002 receives signals from a user 1006. These signals trigger an event in the operating system 1004. The signals are then mapped to an output using the hardware 1008. The output may include audio and video or may be a haptic output including haptic vibration patterns.

Figure 11:
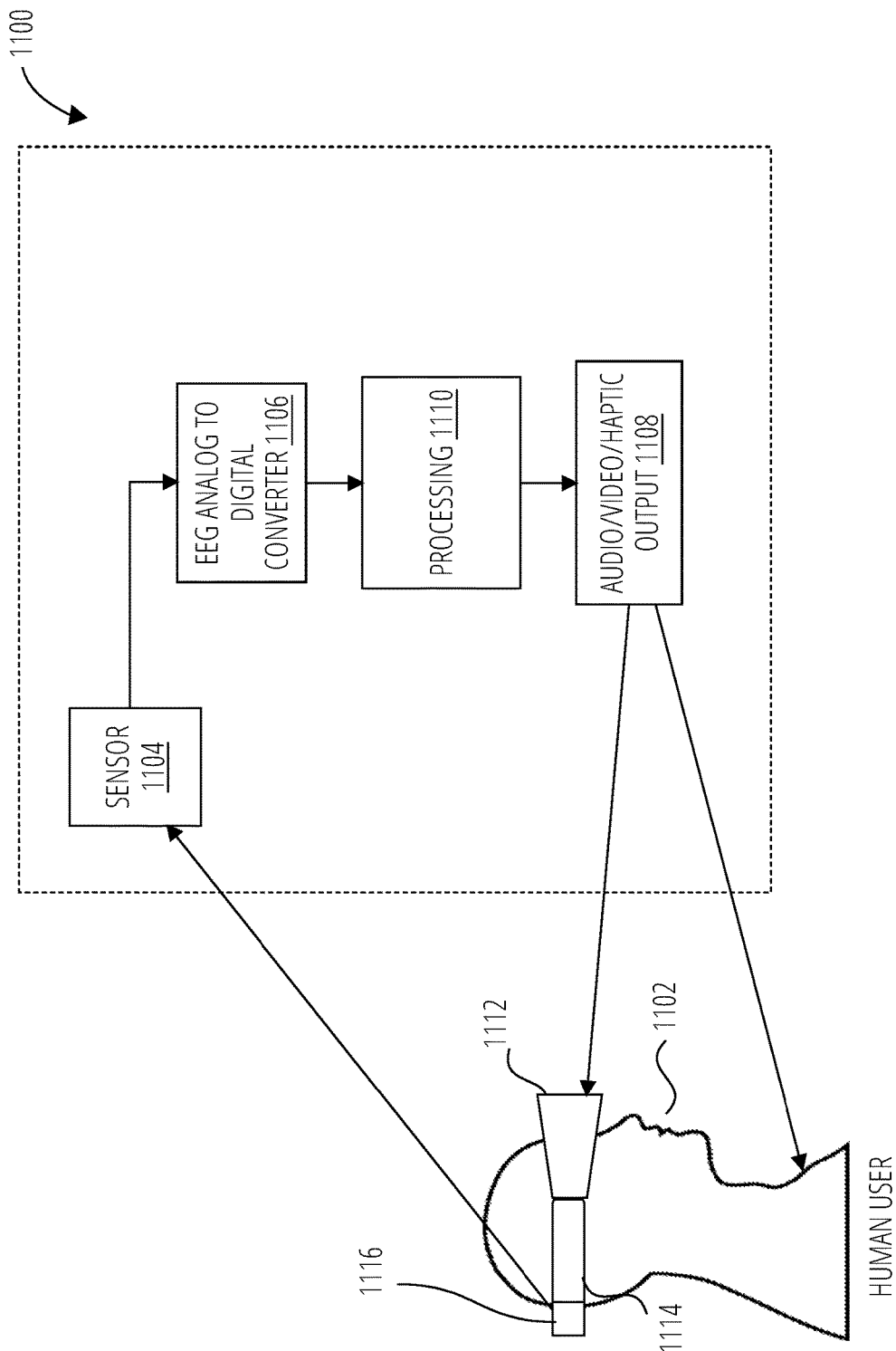
FIG. 11 illustrates a BCI+AR environment 1100 in accordance with one embodiment.

FIG. 11 illustrates an embodiment of a BCI+AR environment 1100. The BCI+AR environment 1100 comprises a sensor 1104, an EEG analog to digital converter 1106, an Audio/Video/Haptic Output 1108, a processing 1110, a strap 1114, an augmented reality glasses 1112, a human user 1102, and a BCI 1116. A human user 1102 is wearing BCI 1116, which is part of a headset. When the human user 1102 interacts with the environment, the sensor 1104, located within the BCI 1116, reads the intentions and triggers the operating system. The EEG analog to digital converter 1106 receives the sensor 1104 output (e.g., intention). EEG analog to digital converter 1106 transforms the sensor output into a digital signal which is sent to processing 1110. The signal is then processed, analyzed and mapped to an Audio/Video/Haptic Output 1108 and displayed on the augmented reality glasses 1112.

In an embodiment, strap 1114 is a head strap for securing the AR+BCI to the human head. In some embodiments, such as an implantable BCI, and AR system, the strap may not be used. The strapless system may use smart glasses or contact lenses. There may be multiple sensors, but no less than one sensor, in different embodiments. After seeing the output, the user may have different bio-signals from the brain, and as such this is a closed-loop biofeedback system. As the user focuses more on the SSVEP stimuli, the audio may feedback by frequency, power (volume), and selected cue audio to assist the human in reinforcing their focus on the stimuli. This may also occur with the vibration type and intensity of the haptics, as well additional peripheral visual cues in the display. These feedbacks are independent to the audio and haptics that may play back through the AR headset via a smartphone. It is even possible to remotely add to the sensory mix that of olfactory (smell) feedback that actually travels through entirely different parts of the brain that has been shown to be one of the strongest bio-feedback reinforcements in human cognitive training.

As a non-limiting example, when someone uses the BCI for the first time, they are considered a "Naïve" user, or one who's brain has never been trained with this kind of user interface. As a user continues to use it, their brain becomes less naïve and more capable and trained. They may become quicker and quicker at doing it. This is reinforcement learning—the BCI enables someone to align their intention and attention to an object and click it.

In an embodiment, to enrich the user interface experience, multiple feedback modalities (auditory, visual, haptic, and olfactory) may be available for choosing the most advantageous feedback modality for the individual or for the type of training. For example, when an appropriate brain wave frequency is generated by the user, real-time feedback about the strength of this signal may be represented by adjusting the intensity and frequency of the audio or haptic feedback. In addition, the possibility of using multimodal feedback means that multiple sensory brain regions are stimulated simultaneously, which enhances the neural signal and representation of feedback, thereby accelerating learning and neural plasticity.

An advantage of using odors as reinforcers may be due to the direct link between the brain areas that sense smell (olfactory cortex) and those that form memories (hippocampus) and produce emotions (amygdala). Odors may strengthen memory encoding, consolidation, and trigger recall.

Figure 12:
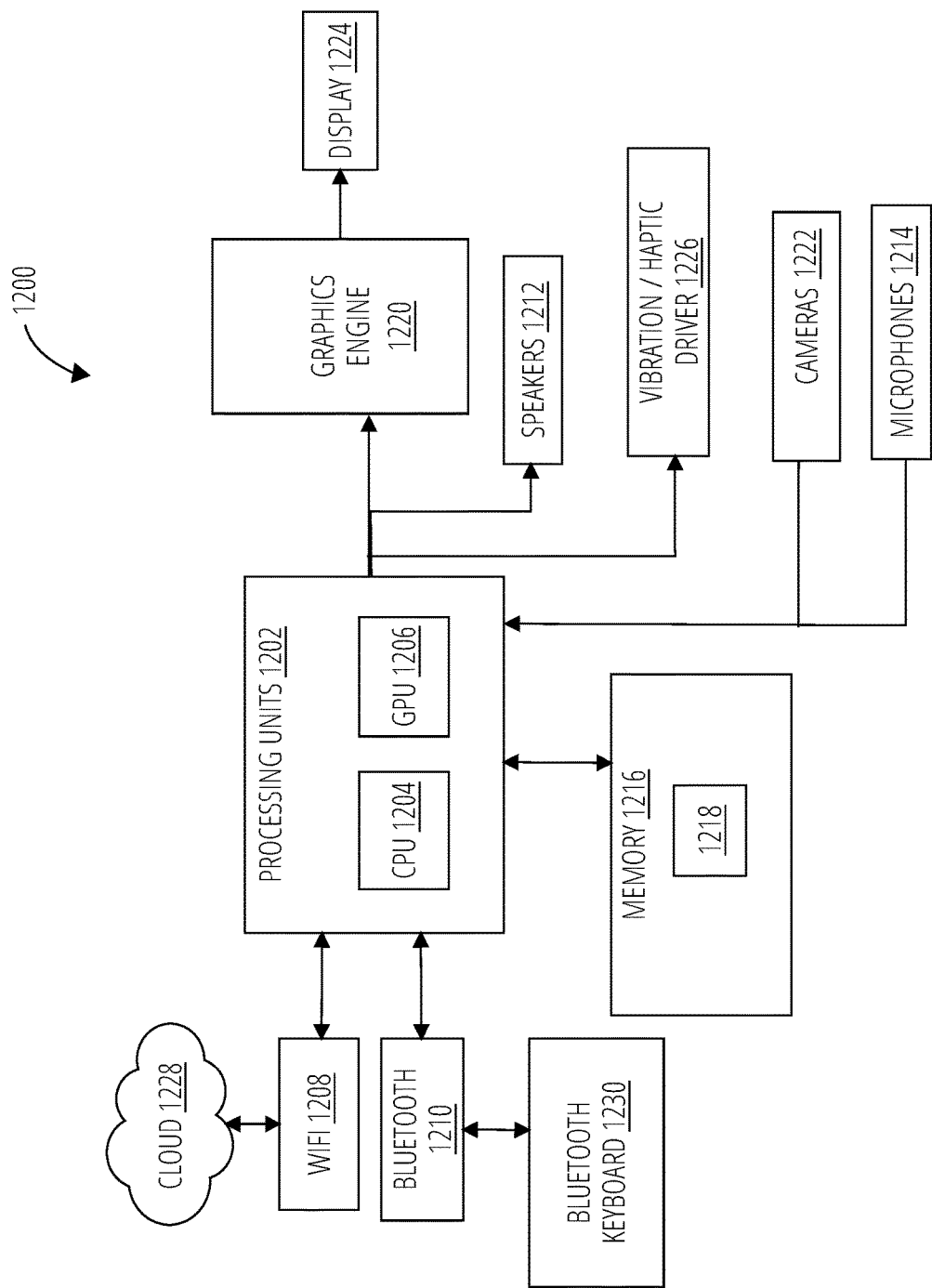
FIG. 12 illustrates an augmented reality device logic 1200 in accordance with one embodiment.

FIG. 12 illustrates components of an exemplary augmented reality device logic 1200. The augmented reality device logic 1200 comprises a graphics engine 1220, a camera 1222, processing units 1202, including one or more CPU 1204 and/or GPU 1206, a WiFi 1208 wireless interface, a Bluetooth 1210 wireless interface, speakers 1212, microphones 1214, one or more memory 1216, logic 1218, a visual display 1224, and vibration/haptic driver 1226.

The processing units 1202 may in some cases comprise programmable devices such as bespoke processing units optimized for a particular function, such as AR related functions. The augmented reality device logic 1200 may comprise other components that are not shown, such as dedicated depth sensors, additional interfaces, etc.

Some or all of the components in FIG. 12 may be housed in an AR headset. In some embodiments, some of these components may be housed in a separate housing connected or in wireless communication with the components of the AR headset. For example, a separate housing for some components may be designed to be worn or a belt or to fit in the wearer's pocket, or one or more of the components may be housed in a separate computer device (smartphone, tablet, laptop or desktop computer etc.) which communicates wirelessly with the display and camera apparatus in the AR headset, whereby the headset and separate device constitute the full augmented reality device logic 1200. A user may also communicate with the AR headset via a Bluetooth keyboard 1230. Additionally, the AR headset may communicate with the cloud 1228 via WiFi 1208.

The memory 1216 comprises logic 1218 to be applied to the processing units 1202 to execute. In some cases, different parts of the logic 1218 may be executed by different components of the processing units 1202. The logic 1218 typically comprises code of an operating system, as well as code of one or more applications configured to run on the operating system to carry out aspects of the processes disclosed herein.

Figure 13:
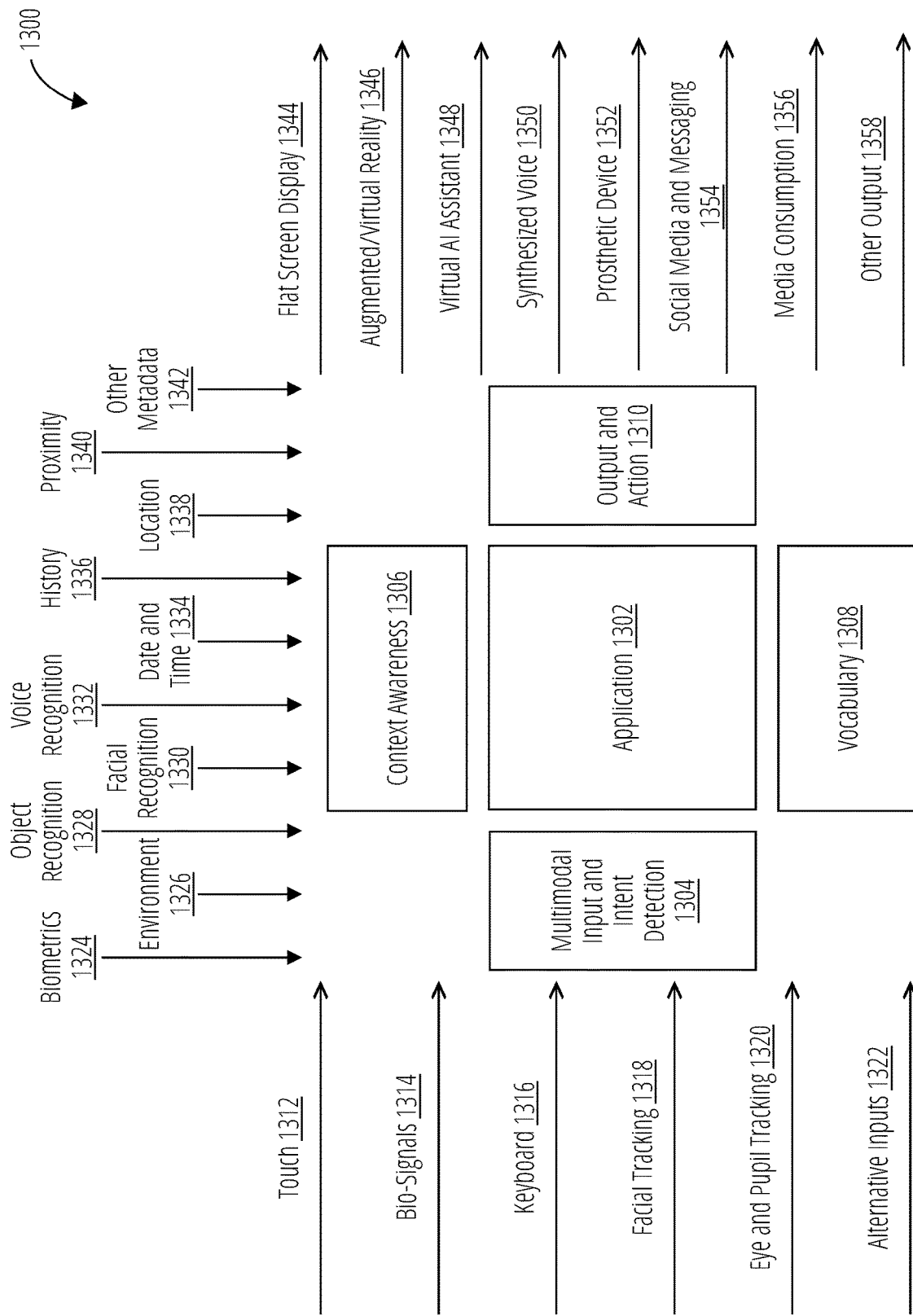
FIG. 13 illustrates a block diagram of nonverbal multi-input and feedback device 1300 in accordance with one embodiment.
Figure 14:
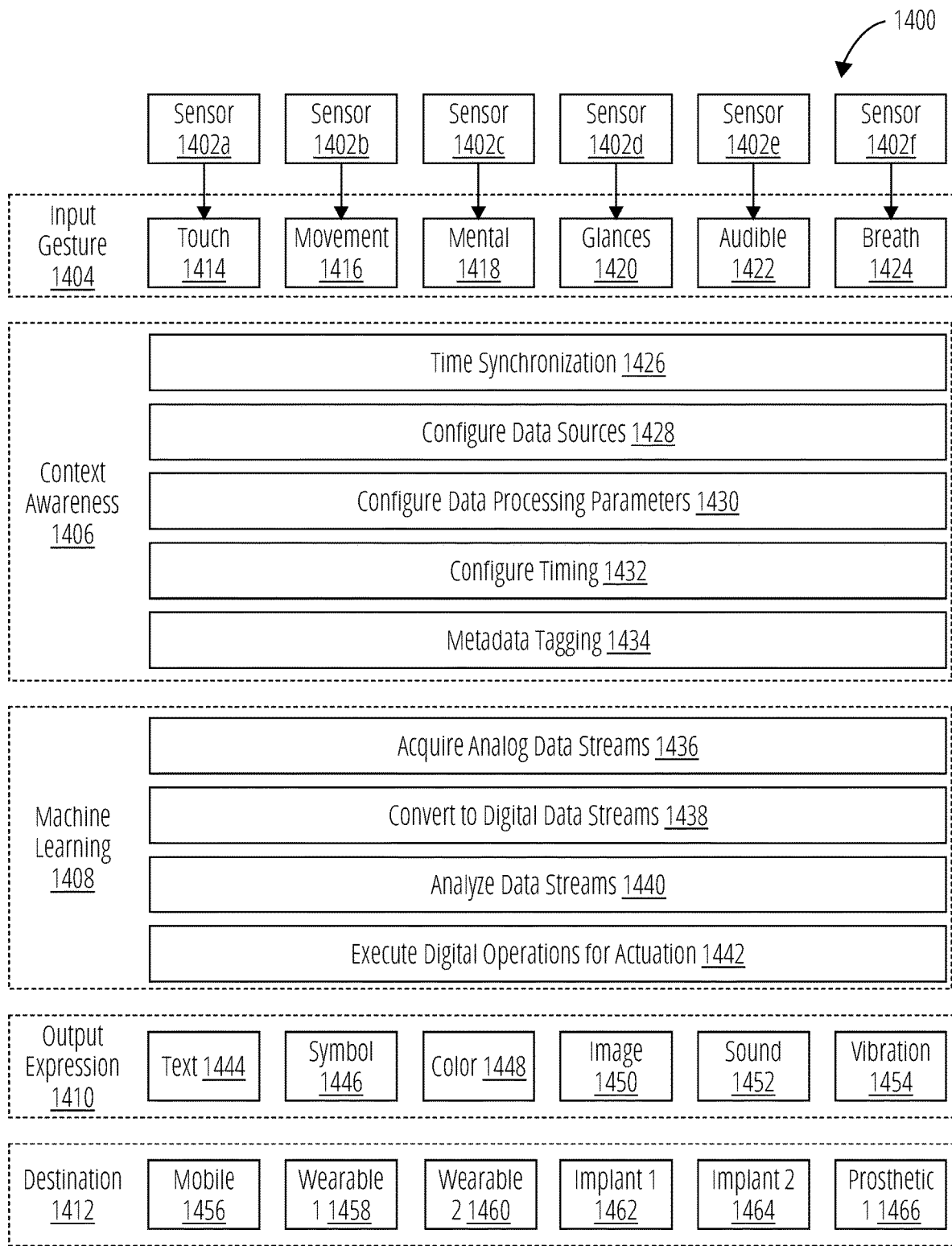
FIG. 14 illustrates a block diagram of a single framework of a nonverbal multi-input and feedback device 1400 in accordance with one embodiment.

FIG. 13 is a block diagram of nonverbal multi-input and feedback device 1300 of a nonverbal multi-input and feedback device such as herein. It may be a block diagram of a portion of the device such as a processing portion of the device. FIG. 13 may be a high-level system architecture block diagram that helps explain that the major building blocks. Block diagram of nonverbal multi-input and feedback device 1300 can be applied to the overall system (e.g., multiple devices used as inputs), into a common universal application interface that enables the application 1302 to synchronize data coming from multiple devices and process signals with meta data, plus vocabulary and output logic to a plurality of output methods. FIG. 14 takes this to a finer level of detail.

In the center of block diagram of nonverbal multi-input and feedback device 1300 is the application 1302 or main processing block. To the left is the multimodal input and intent detection 1304 block which receives and processes user inputs from sensors (e.g., based on user input received by the sensors) such as touch 1312; bio-signals 1314; keyboard 1316; facial tracking 1318; eye and pupil tracking 1320; and alternative inputs 1322. This multimodal input and intent detection 1304 block feeds the processing from these inputs to the application 1302.

Above is a context awareness 1306 block which receives and processes metadata inputs from sensors such as biometrics 1324; environment 1326; object recognition 1328; facial recognition 1330; voice recognition 1332; date and time 1334; history 1336; location 1338; proximity 1340; and other metadata 1342 inputs. This context awareness 1306 block feeds the processing from these inputs to the application 1302.

To the right is an output and action 1310 block which sends outputs to displays, computing devices, controllers, speakers and network communication devices such as flat screen flat screen display 1344; augmented/virtual reality 1346; virtual AI assistant 1348; synthesized voice 1350; prosthetic device 1352; social media and messaging 1354; media consumption 1356; and other output 1358. The outputs may include control commands and communication sent to other computing devices. they may include text, graphics, emoji, and/or audio. Other output 1358 may include Robots, Drones, Swarms and other semi-autonomous systems; Mobility Systems & Vehicle controls such as wheelchairs, automobiles and aircraft; and Environmental connected systems such as smart buildings, spacecraft or submersibles.

Figure 20:
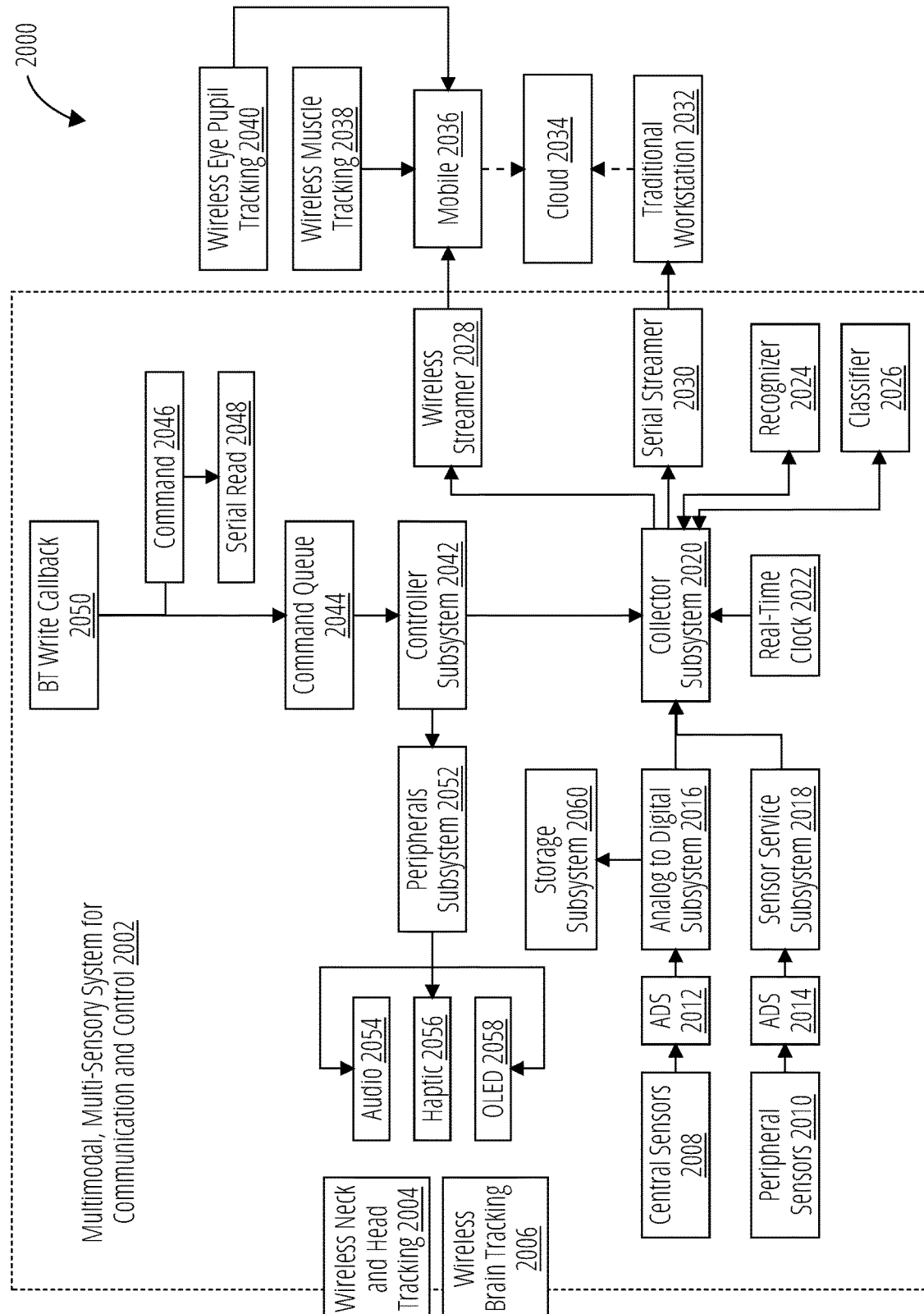
FIG. 20 illustrates a flow diagram 2000 in accordance with one embodiment.

Below is a vocabulary 1308 block that provides a lexicon or vocabulary in the selected language to the application. FIG. 13 may also be applied to a single sensory device unto itself. This may be a "BIG IDEA" in so far as the architecture can scale from a single closed-loop system (such as in FIGS. 13-17, plus 19) as well as combinations of sensory I/O devices (FIGS. 12, 18, 20). It may be a system of systems that scale up, down and play together.

Figure 16:
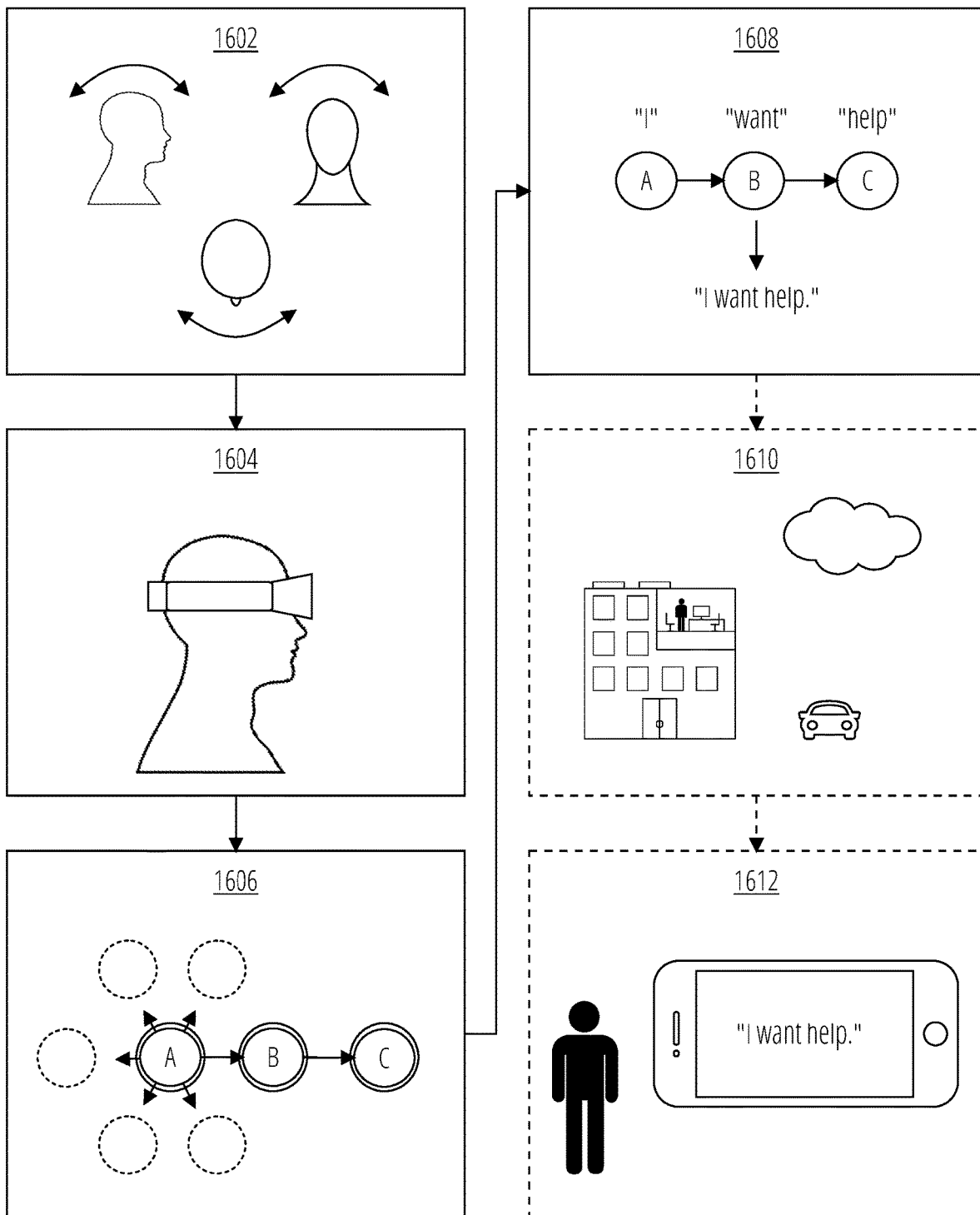
FIG. 16 illustrates a logical diagram of a user wearing an augmented reality headset in accordance with one embodiment.

The system in block diagram of nonverbal multi-input and feedback device 1300 comprises one (or more) sensory input, one intent detection API, one application, one (or more) meta data, one (or more) vocabulary, one (or more) output and action method, and one (or more) output/actuation system or device. It may be thought of as a universal "augmented intelligence" engine that takes inputs, enriches them with extra meaning, and directs the output based on instructions for the enriched information. The storyboard in FIG. 16 illustrates the power of this.

In a simple embodiment of diagram 1010, a user sees a symbol or button that means "help", and presses it, and the device says "help". In a more complicated embodiment of block diagram of nonverbal multi-input and feedback device 1300, a user sees a symbol or button that means "help", and press it. Here, rather than the device saying "help", it learns that the user is connected to a caregiver with logic to send urgent matters to that person via text or instant message when away from home. The device may geolocation data that indicates the user is away from home; tag the communication with appended contextual information; and its output and action logic tell the system to send a text message to the caregiver with the user's location in a human-understandable grammatically correct phrase "Help, I'm in Oak Park" including the user's Sender ID/Profile and coordinates pinned on a map.

FIG. 14 is a block diagram of a single framework of a nonverbal multi-input and feedback device 1400 such as herein. The block diagram of a single framework of a nonverbal multi-input and feedback device 1400 may be of a single framework for translating diverse sensor inputs into a variety of understandable communication and command outputs for a nonverbal multi-input and feedback device such as herein. The single framework of a nonverbal multi-input and feedback device comprises sensors 1402a-1402f, input gestures 1404, context awareness 1406, machine learning 1408, output expressions 1410, and destinations 1412. Input gestures 1404 may include touch 1414, movement 1416, mental 1418, glances 1420, audible 1422, and breath 1424. Context awareness 1406 may include time synchronization 1426, configure data sources 1428, configure data processing parameters 1430, configure timing 1432, and metadata tagging 1434. Machine learning 1408 may include an acquire analog data streams 1436, convert to digital data streams 1438, analyze data streams 1440, and execute digital operations for actuation 1442. Output expressions 1410 may include text 1444, symbol 1446, color 1448, an image 1450, sound 1452, and vibration 1454. Destinations 1412 may include a mobile 1456, a wearable 1 1458, a wearable 2 1460, an implant 1 1462, an implant 2 1464, and a prosthetic 1 1466.

FIG. 14 may describe in more detail what kind of processing is happening within and across the blocks of FIG. 13. Specifically, the left intention signals being combined with context awareness metadata to enrich the data in order to determine the logic of the output and action. FIG. 14 may include the description of the Vocabulary 1308 and application 1302 boxes of FIG. 13, though not shown. It may be a block diagram of a portion of the device such as a processing portion of the device. In the framework, input from the sensors 1402a-1402f (e.g., due to input received by the sensors) are received by or as an input gesture 1404. In the framework, context awareness 1406 awareness is used to interpret or determine the user gesture or intent from the inputs received. In the framework machine learning 1408 is used to interpret or determine the user gesture or intent from the inputs received. In the framework, output expression 1410 is used to determine the outputs, such as control commands and communication sent to other computing devices that include text, graphics, emoji, and/or audio. In the framework, destination 1412 is used to determine where the outputs are sent, such as to what other computing devices the command and/or communications are to be sent (such as by the network). The user's Primary and Secondary language preferences are accessed during the processing of intention data which is stored in the vocabulary 1308 subsystem such as shown in FIG. 13, and may be accessed in the context awareness 1406, machine learning 1408 and output and action 1310 systems and methods in FIG. 13 and FIG. 14.

Figure 15:
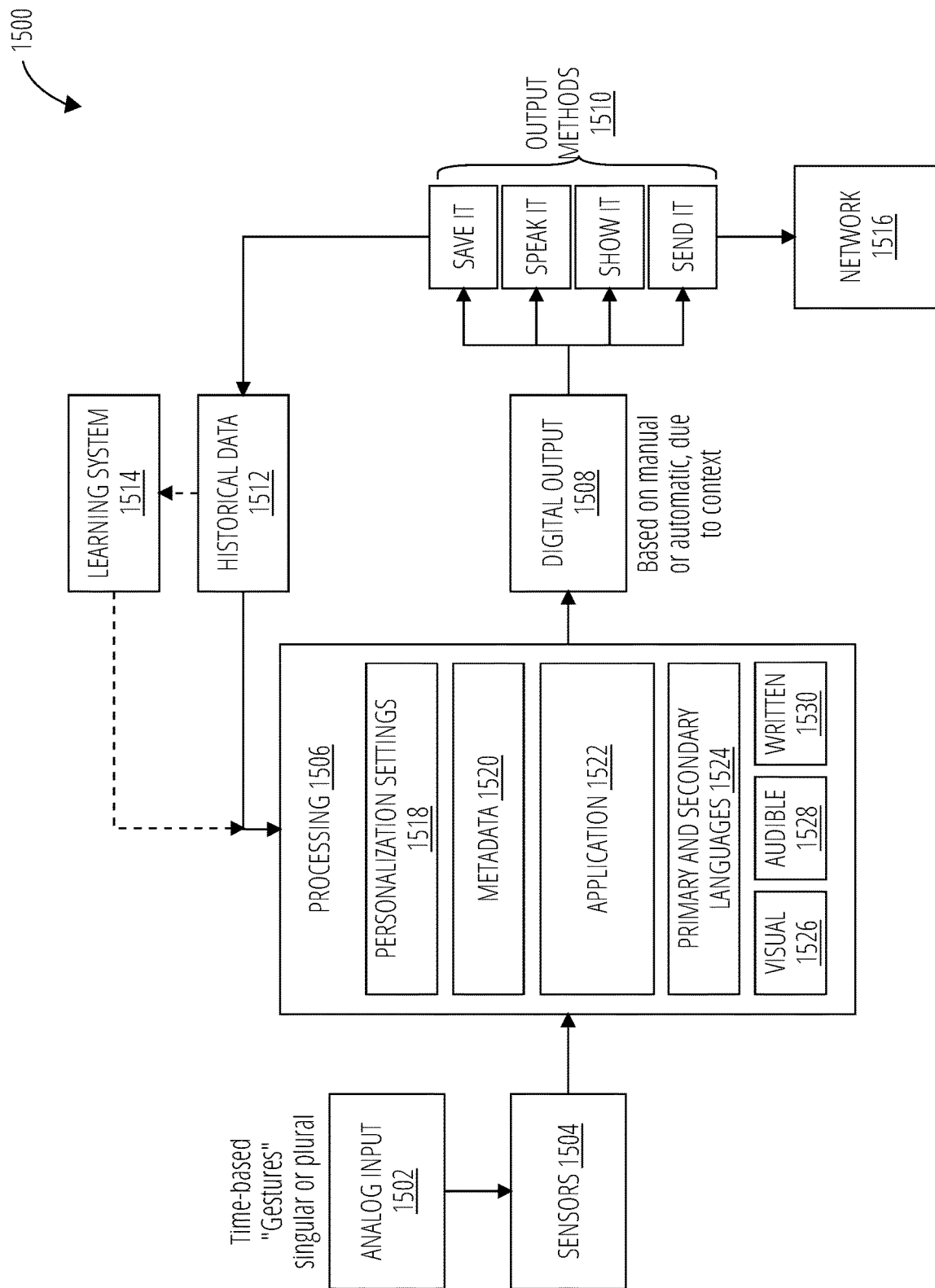
FIG. 15 illustrates a block diagram of nonverbal multi-input and feedback device 1500 in accordance with one embodiment.

FIG. 15 illustrates a block diagram of nonverbal multi-input and feedback device 1500 in one embodiment. The block diagram of nonverbal multi-input and feedback device 1500 shows a system comprising analog input 1502, sensors 1504, processing 1506, digital output 1508, and output methods 1510 that may be performed with the digital output 1508.

The system illustrated may include an application programming interface (API) that is interoperable with multiple types of analog input 1502 from the sensors 1504. The system illustrated may also comprise a real-time clock for tracking, synchronizing, and metadata 1520 tagging of data streams and analog inputs 1502. The system further comprises a subsystem for data storage and management, for historical data 1512 in some embodiments. The system may comprise a subsystem for personalization settings 1518, as well as a subsystem for sourcing and integrating metadata 1520 into the application 1522 and data stream. The system may further comprise a software application 1522. In some embodiments, the system may include a GUI for the software application for the user. In other embodiments, the system may include a GUI for the software application for others who are connected to a system user.

A subsystem of the system may include processing for visual 1526, audible 1528, and written 1530 languages. This language subsystem may differentiate between the user's primary and secondary languages 1524. The language subsystem may set the secondary language manually or automatically. Attributes processed by visual 1526, audible 1528, and written 1530 language subsystems may include but not be limited to color, image, graphics, audible tones, phonemes, dialects, jargon, semantics, tonality, and written characters.

The system may include a subsystem of digital outputs 1508 and output methods 1510, that can be configured either manually or automatically. The variety of output methods 1510 may include a network 1516 interface connection. The system may comprise a subsystem for managing data transfer over the network 1516.

The system in some embodiments may comprise a historical data 1512 subsystem for closed-loop machine learning of the system and subsystems and the sensory devices being used with the system. In some embodiments, improved models, algorithms and software may be pushed from the learning system 1514 to update and be used within the system and subsystems and the sensory devices being used with the system In one embodiment, the system and subsystems may operate entirely on a sensory device. In one embodiment, the system and subsystems may operate partially on a sensory device and partially distributed to other devices or the cloud. In one embodiment, the system and subsystems may operate entirely distributed on other devices or the cloud.

The system of FIG. 15 may be one embodiment of a fully self-contained brain computer interface (BCI) in a wireless headset, comprising an augmented reality display as part of the digital output 1508, at least two sensors 1504 for reading a bio-signal from a user as analog input 1502, at least one processing 1506 module for the augmented reality display, at least one biofeedback device that produces at least one of a visual, audible, and tactile effect in communication with the processing module to provide feedback to the user, a wireless network interface that transmits and receives data to and from other devices over the processing 1506, wherein the data is at least one of stored, passed through, and processed on the fully self-contained BCI, as part of the output methods 1510, a battery, wherein the battery provides power to one or more of the augmented reality display, the at least two sensors, the processing module, and the at least one biofeedback device, at least one of onboard storage or remote storage with enough memory to store, process and retrieve the data, and a printed circuit board, such as the printed circuit board 902 introduced in FIG. 9.

Bio-signals from the user may comprise at least one of EEG (Electroencephalography), ECG (Electrocardiography), functional near infrared spectroscopy (fNIRS), Magnetoencephalography (MEG), EMG (Electromyography), EOG (Electroocculography), and Time-Domain variants (TD-) of these bio-signal processing methods. Bio-signals may also comprise a visually evoked potential, an audio evoked potential, a haptic evoked potential, and a motion evoked potential, and other bio-signals from multiple sources attached to other body parts other than a user's head.

The at least one processing module for the augmented reality display may include a processor that renders a stimulation effect. This stimulation effect may be at least one of a timed visual stimulation on the augmented reality display, a timed audio stimulation, and a haptic stimulation on the fully self-contained BCI configured to evoke a measurable response in a user's brain. The processing module may include a processor that analyzes and maps the bio-signal into a digital command. This digital command may include least one of instructions for a visual output configured for displaying on the augmented reality display and instructions for triggering a visual effect. The processing module may be embodied as the processing units 1202 introduced in FIG. 12.

The printed circuit board may include at least one of the at least two sensors, the processing module, the at least one biofeedback device, the battery, and combinations thereof. The printed circuit board may be configured to emulate a Bluetooth keyboard and send output data to at least one of a mobile device, a computer, and the augmented reality display. The output data may include at least one of a letter, a character, a number, and combinations thereof.

Processing performed by the processing module may include the visually evoked potential, the audio evoked potential, and the haptic evoked potential. The bio-signal is processed and analyzed in real-time. The processing module may have different modes, including raw, simmer, and cooked modes, a human interface device-keyboard mode, and combinations thereof. The system may also have a strapless mode, wherein the fully self-contained BCI uses smart glasses or smart contact lenses, an implantable brain computer interface, and an AR system.

The raw mode may stream a full EEG sensor stream of data for further processing locally on device or remotely in a cloud via a mobile or desktop internet connected device that may filter, recognize, or interact with the full EEG sensor stream of data. The cooked mode may comprise a fully processed custom digital command generated by a local recognizer and classifier. The fully processed custom digital command may be sent to a destination system over the network 1516, per the "send it" output method 1510, and executed on the destination system, with no raw data passed to the user. The recognizer and classifier may be embodied as the recognizer 2024 and classifier 2026 introduced in FIG. 20. The simmer mode may be a hybrid combination between the raw mode and the cooked mode, and the at least one processing module may intersperse a raw data stream with cooked metadata 1520 appended to bio-signal data.

Time domain data may be appended to raw data, cooked data, and simmer data in order for the system to process bio-signal data streams from multiple bio-signal data sources and ensure all bio-signal data streams are synchronized. Metadata from other sensors and data sources may be appended to the raw data, the cooked data, and the simmer data in order for a classifier to alter the command that is sent to execute on a destination system. This classifier may be embodied as the classifier 2026 introduced in FIG. 20. Visual, audible, and tactile sensory frequency stimulators may be appended with metadata from other sensors 1504 and data sources wherein the visual, audible, and tactile sensory frequency stimulators are altered to produce a unique pattern which includes metadata that is decodable by the recognizer and classifier.

The fully self-contained BCI may be electrically detached from the augmented reality display, and may be configured to transfer data wirelessly or via a wired connection to an external augmented reality display. The fully self-contained BCI in the wireless headset may be an accessory apparatus that is configured to be temporarily mechanically integrated with another wearable device, and configured to transfer data wirelessly or via a wired connection to the other wearable device. The fully self-contained BCI may in another embodiment be permanently mechanically integrated with another wearable device and may transfer data wirelessly or via a wired connection to the other wearable device.

A charging port may be connected to a charging bridge, wherein the charging bridge includes internal circuitry and data management connected to the fully self-contained BCI and the augmented reality display. The internal circuitry may include charging circuitry, thereby allowing charging of both the fully self-contained BCI and the augmented reality display with the charging circuitry. These functions may in some embodiments be carried out by the USB/TTL bridge 928 and power management module 934 introduced in FIG. 9.

The fully self-contained BCI may be configured to generate visual, auditory, or haptic stimulations to a user's visual cortex, a user's auditory cortex, and a user's somatosensory cortex, thereby resulting in detectable brain wave frequency potentials that are at least one of stimulated, event-related, and volitionally evoked. The BCI may process the detectable brain wave frequencies, thereby facilitating mapping of bio-signals to digital commands. Stimulation effects and digital commands may be altered with metadata from other sensors or data sources.

The BCI may synchronize bio-signal processing from multiple sensors with a real-time clock such as the real-time clock 2022 introduced in FIG. 20. Digital commands may be associated to a device. The device may be operated according to the digital commands. The BCI may stimulate the user's visual cortex, wherein stimulating includes biofeedback to the user's visual cortex and biofeedback confirmation of the operating of the device. The BCI may stimulate the user's somatosensory cortex, wherein stimulating includes the biofeedback confirmation of the operating of the device. The BCI may stimulate the user's auditory cortex, wherein the stimulating includes biofeedback confirmation of the operating of the device.

The fully self-contained BCI may be configured to utilize AI machine learning for pattern recognition, classification, and personalization that operates while the fully self-contained BCI is not connected to a network 1516. The AI machine learning may be embodied as the machine learning 1408 introduced in FIG. 14. It may be included in the learning system 1514 of this figure. It may also be supported by the machine learning capture and modeling 1910 and machine learning parameters 1924 introduced in FIG. 19. The AI machine learning may act as one or more of an auto-tuning dynamic noise reducer, a feature extractor, and a recognizer-categorizer-classifier. AI machine learning training may be applied when the fully self-contained BCI is connected to the network 1516 to create an individualized recognizer-categorizer-classifier. Derived outputs of the AI machine learning training may be stored in an expert system knowledge base in cloud storage or on a mobile computing device having at least one of a wireless connection and a wired connection to the wireless headset and being at least one of mounted on the wireless headset and within wireless network range of the wireless headset. Synthesized insights derived from the AI machine learning and the expert system knowledge base may be stored in cloud storage or on the mobile computing device and may be used to generate an individualized executable recognizer-categorizer-classifier downloadable onto the at least one processing 1506 module of the fully self-contained BCI or the mobile computing device via at least one of a wireless connection and a wired connection between the network and a BCI storage device for offline usage without network dependencies. The system may be configured to interface with resource constrained devices including wearable devices, implantable devices, and internet of things (IoT) devices. At least one biofeedback device may be configured to stimulate at least one of a user's central nervous system and peripheral nervous system.

FIG. 16 illustrates a logical diagram of one use case of a user wearing an augmented reality headset that includes a display, speakers and vibration haptic motors and an accelerometer/gyroscope and magnetometer. FIG. 16 shows the flow of activity from head motion analog input 1602 as captured by a headset with head motion detection sensors 1604, through how a user selects options through head motion 1606 and the application creates output based on the user's selected options 1608. On the condition that system detects the user is away from home 1610, FIG. 16 shows that the system may send output to a caregiver via text message 1612.

The user may calibrate the headset based on the most comfortable and stable neck and head position which establishes the X/Y/Z position of 0/0/0. Based on this central ideal position, the user interface is adjusted to conform to the user's individual range of motion, with an emphasis of reducing the amount of effort and distance needed to move a virtual pointer in augmented reality from the 0/0/0 position to outer limits of their field of view and range of motion. The system may be personalized with various ergonomic settings to offset and enhance the users ease of use and comfort using the system. A head motion analog input 1602 may be processed as analog streaming data and acquired by the headset with head motion detection sensors 1604 in real-time, and digitally processed, either directly on the sensory device or via a remotely connected subsystem. The system may include embedded software on the sensory device that handles the pre-processing of the analog signal. The system may include embedded software that handles the digitization and post-processing of the signals. Post-processing may include but not be limited to various models of compression, feature analysis, classification, metadata tagging, categorization. The system may handle preprocessing, digital conversion, and post-processing using a variety of methods, ranging from statistical to machine learning. As the data is digitally post-processed, system settings and metadata may be referred to determine how certain logic rules in the application are to operate, which may include mapping certain signal features to certain actions. Based on these mappings, the system operates by executing commands and may include saving data locally on the sensory device or another storage device, streaming data to other subsystems or networks.

In the case illustrated in FIG. 16, the user is looking at a display that may include characters, symbols, pictures, colors, videos, live camera footage or other visual, oral or interactive content. In this example, the user is looking at a set of "radial menus" or collection of boxes or circles with data in each one that may be a symbol, character, letter, word or entire phrase. The user has been presented a set of words that surround a central phrase starter word in the middle like a hub and spoke to choose from based on typical functional communication with suggested fringe words and access to predictive keyboard, structured and unstructured language. The user selects options through head motion 1606, and may rapidly compose a phrase by selecting the next desired word presented in the radial menus, or adding a new word manually via another input method. The user traverses the interface using head movement gestures, similar to 3-dimensional swipe movements, to compose communication. The user progressively chooses the next word until they're satisfied with the phrase they've composed and can determine how to actuate the phrase. Algorithms may be used to predict the next character, word, or phrase, and may rearrange or alter the expression depending on it's intended output including but not limited to appending emoji, symbols, colors, sounds or rearranging to correct for spelling or grammar errors. The user may desire for the phrase to be spoken aloud to a person nearby, thus selecting a "play button" or simply allowing the sentence to time out to be executed automatically. The application creates output based on the user's selected options 1608. If they compose a phrase that is a control command like "turn off the lights", they can select a "send button" or may, based on semantic natural language processing and understanding, automatically send the phrase to a third party virtual assistant system to execute the command, and turn off the lights. The potential use of metadata, in this example, could simply be geolocation data sourced from other systems such as GIS or GPS data or WIFI data, or manually personalized geofencing in the application personalization settings, where the system would know if the user is "at home" or "away from home". On condition that system detects the user is away from home 1610, for example, the metadata may play a role in adapting the language being output to reflect the context of the user. For instance, the system could be configured to speak aloud when at home but send output to a caregiver via text message 1612 and append GPS coordinates when away from home. The system may support collecting and processing historical data from the sensory device, system, subsystems, and output actions to improve the performance and personalization of the system, subsystems, and sensory devices.

Figure 17:
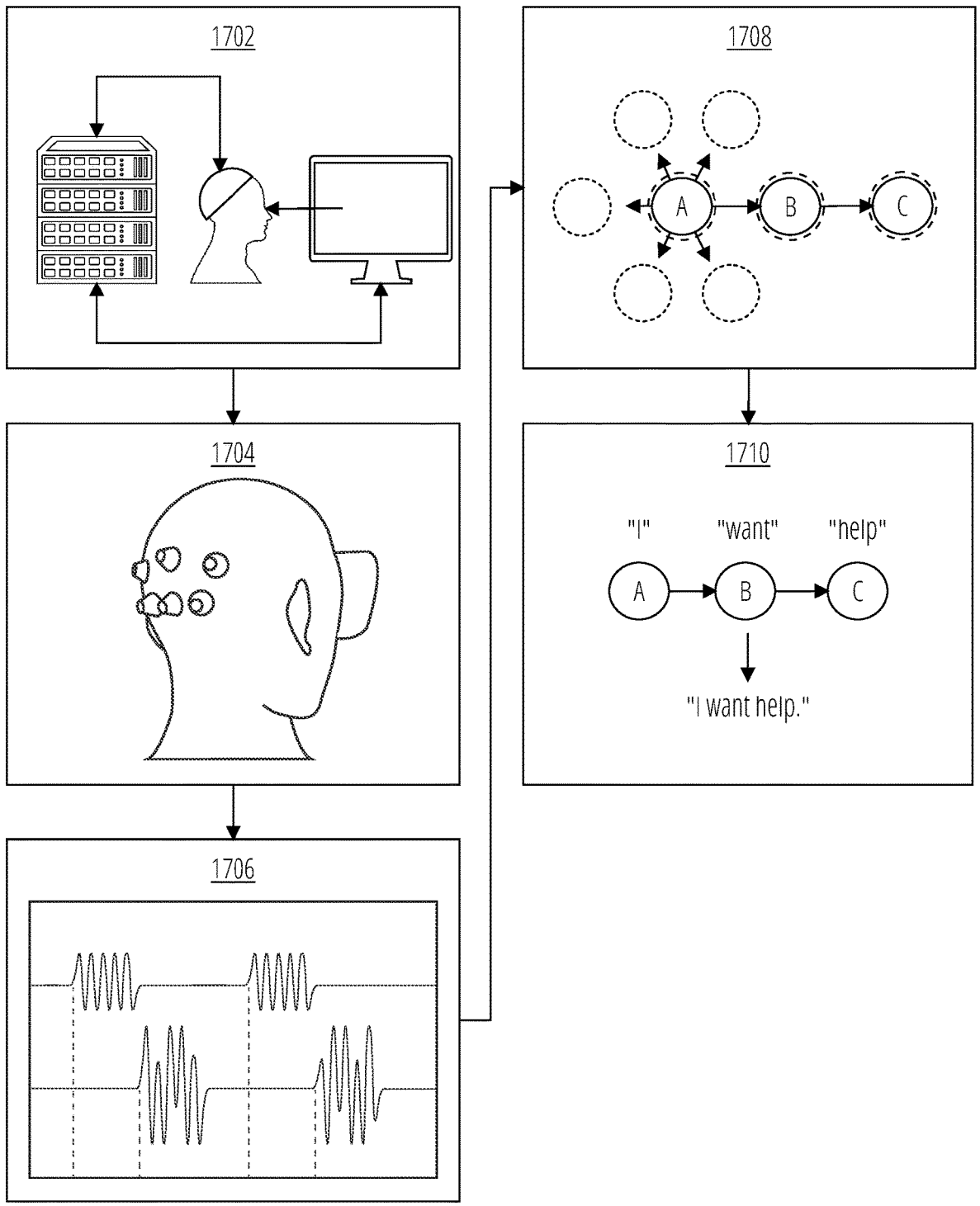
FIG. 17 a logical diagram of a user wearing an augmented reality headset in accordance with one embodiment.
Figure 18:
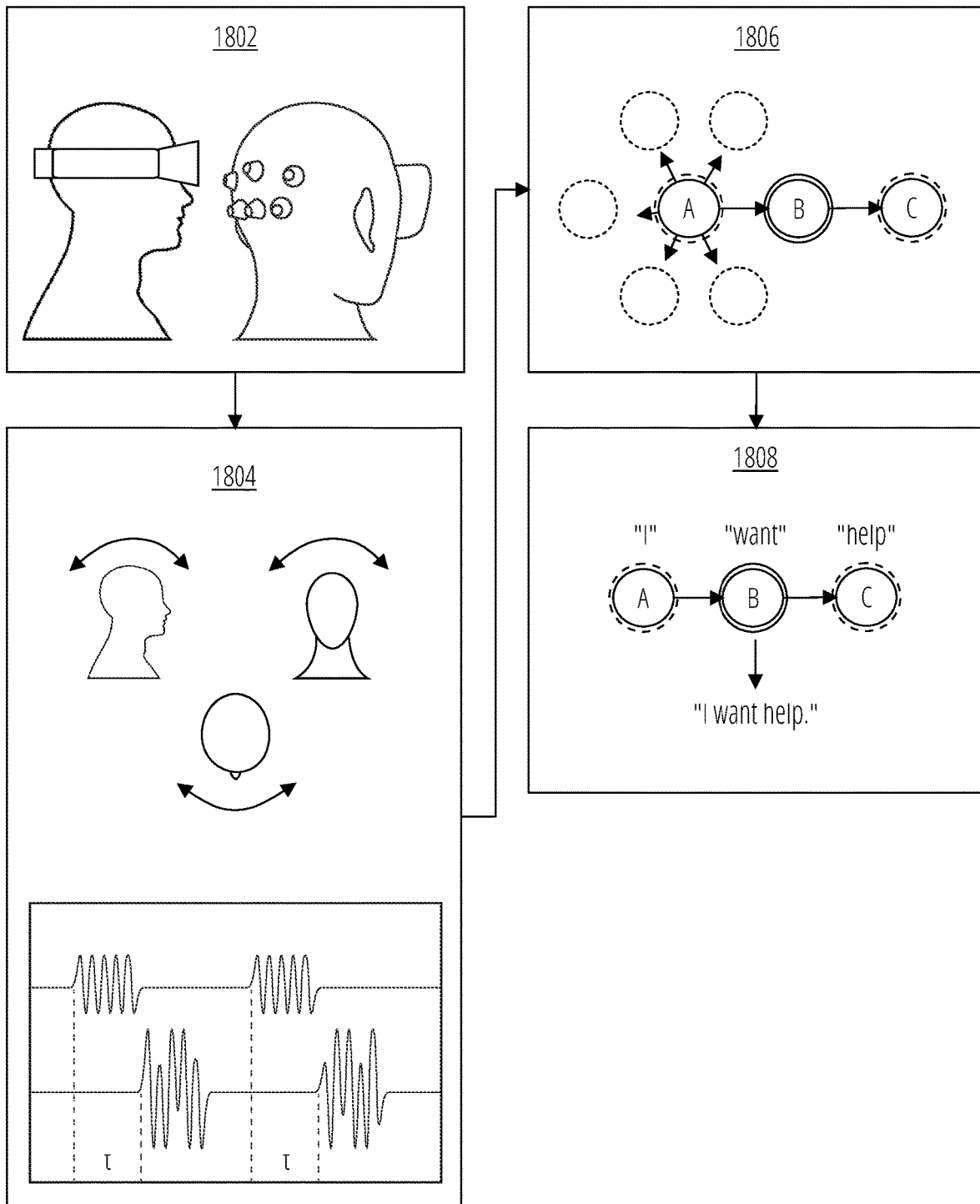
FIG. 18 illustrates a diagram of a use case including a user wearing an augmented reality headset in accordance with one embodiment.

FIG. 17 illustrates a logical diagram of one use case in which user wears an EEG-based brain-computer interface headset 1702 containing electrodes that are contacting the scalp 1704. FIG. 17 shows that streaming analog data can be acquired from the brainwave activity 1706. In this manner, the user may be presented a set of words to choose from 1708, compose a phrase, and select what action the system takes using the phrase they've composed 1710.

A user wears an EEG-based brain-computer interface headset 1702 containing electrodes that are contacting the scalp 1704. The electrodes are connected to an amplifier and analog-to-digital processing pipeline. The sensory device (BCI) acquires streaming electrical current data measured in microvolts (mV). The more electrodes connected to the scalp and to the BCI, the more streaming analog data can be acquired from the brainwave activity 1706. The analog streaming data is acquired by the electrodes, pre-processed through amplification, and digitally processed, either directly on the sensory device or via a remotely connected subsystem. The system may include embedded software on the sensory device that handles the pre-processing of the analog signal. The system may include embedded software that handles the digitization and post-processing of the signals. Post-processing may include but not be limited to various models of compression, feature analysis, classification, metadata tagging, categorization. The system may handle preprocessing, digital conversion, and post-processing using a variety of methods, ranging from statistical to machine learning. As the data is digitally post-processed, system settings and metadata may be referred to determine how certain logic rules in the application are to operate, which may include mapping certain signal features to certain actions. Based on these mappings, the system operates by executing commands and may include saving data locally on the sensory device or another storage device, streaming data to other subsystems or networks.

In the case illustrated in FIG. 17, the user is looking at a display that may include characters, symbols, pictures, colors, videos, live camera footage or other visual, oral or interactive content. In this example, the user is looking at a group of concentric circles, arranged in a radial layout, with characters on each circle. The user has been presented a set of words to choose from 1708 based on typical functional communication with suggested fringe words and access to predictive keyboard and can rapidly compose a phrase by selecting the next desired word presented in the outer ring of circles, or adding a new word manually. The user progressively chooses the next word until they're satisfied with the phrase they've composed 1710 and can determine how to actuate the phrase. Algorithms may be used to predict the next character, word, or phrase, and may rearrange or alter the expression depending on its intended output including but not limited to appending emoji, symbols, colors, sounds or rearranging to correct for spelling or grammar errors. The user may desire for the phrase to be spoken aloud to a person nearby, thus selecting a "play button" or simply allowing the sentence to time out to be executed automatically. If they compose a phrase that is a control command like "turn off the lights", they can select a "send button" or may, based on semantic natural language processing and understanding, automatically send the phrase to a third party virtual assistant system to execute the command, and turn off the lights. The potential use of metadata, in this example, could simply be geolocation data sourced from other systems such as GIS or GPS data or WIFI data, or manually personalized geofencing in the application personalization settings, where the system would know if the user is "at home" or "away from home". In this case, the metadata may play a role in adapting the language being output to reflect the context of the user. For instance, the system could be configured to speak aloud when at home but send to a caregiver via text message and append GPS coordinates when away from home. The system may support collecting and processing historical data from the sensory device, system, subsystems, and output actions to improve the performance and personalization of the system, subsystems, and sensory devices.

FIG. 18 illustrates a use case in which a user wears an augmented reality headset combined with a brain computer interface 1802, having the capabilities described with respect to FIG. 16 and FIG. 17. Both head motion analog input and brainwave activity 1804 may be detected and may allow a user to select from a set of words to choose from 1806, as well as what to do with the phrase they've composed 1808 by selecting those words.

A user is wearing an augmented reality headset combined with a brain computer interface on their head. The headset contains numerous sensors as a combined sensory device including motion and orientation sensors and temporal bioelectric data generated from the brain detected via EEG electrodes contacting the scalp of the user, specifically in the regions where visual, auditory and sensory/touch is processed in the brain. The AR headset may produce visual, auditory or haptic stimulation that is detectible via the brain computer interface, and by processing brainwave data with motion data, the system may provide new kinds of multimodal capabilities for a user to control the system. The analog streaming data is acquired by the Accelerometer, Gyroscope, Magnetometer and EEG analog-to-digital processor, and digitally processed, either directly on the sensory device or via a remotely connected subsystem. The system may include embedded software on the sensory device that handles the pre-processing of the analog signal. The system may include embedded software that handles the digitization and post-processing of the signals. Post-processing may include but not be limited to various models of compression, feature analysis, classification, metadata tagging, categorization. The system may handle preprocessing, digital conversion, and post-processing using a variety of methods, ranging from statistical to machine learning. As the data is digitally post-processed, system settings and metadata may be referred to determine how certain logic rules in the application are to operate, which may include mapping certain signal features to certain actions. Based on these mappings, the system operates by executing commands and may include saving data locally on the sensory device or another storage device, streaming data to other subsystems or networks.

In the case illustrated in FIG. 18, the user is looking at a display that may include characters, symbols, pictures, colors, videos, live camera footage or other visual, oral or interactive content. In this example, the user is looking at a visual menu system in AR with certain hard to reach elements flickering at different frequencies. The user has been presented a set of items to choose from based on typical functional communication with suggested fringe words and access to predictive keyboard and can rapidly compose a phrase by selecting the next desired word presented in the AR head mounted display, or adding a new word manually. Enabling the user affordances of extra-sensory reach of visible objects out of reach within the comfortable range of motion of neck movement. The user progressively chooses the next word until they're satisfied with the phrase they've composed and can determine how to actuate the phrase. Algorithms may be used to predict the next character, word, or phrase, and may rearrange or alter the expression depending on its intended output including but not limited to appending emoji, symbols, colors, sounds or rearranging to correct for spelling or grammar errors. The user may desire for the phrase to be spoken aloud to a person nearby, thus selecting a "play button" or simply allowing the sentence to time out to be executed automatically. If they compose a phrase that is a control command like "turn off the lights", they can select a "send button" or may, based on semantic natural language processing and understanding, automatically send the phrase to a third party virtual assistant system to execute the command, and turn off the lights. The potential use of metadata, in this example, could simply be geolocation data sourced from other systems such as GIS or GPS data or WIFI data, or manually personalized geofencing in the application personalization settings, where the system would know if the user is "at home" or "away from home". In this case, the metadata may play a role in adapting the language being output to reflect the context of the user. For instance, the system could be configured to speak aloud when at home but send to a caregiver via text message and append GPS coordinates when away from home. The system may support collecting and processing historical data from the sensory device, system, subsystems, and output actions to improve the performance and personalization of the system, subsystems, and sensory devices.

Figure 19:
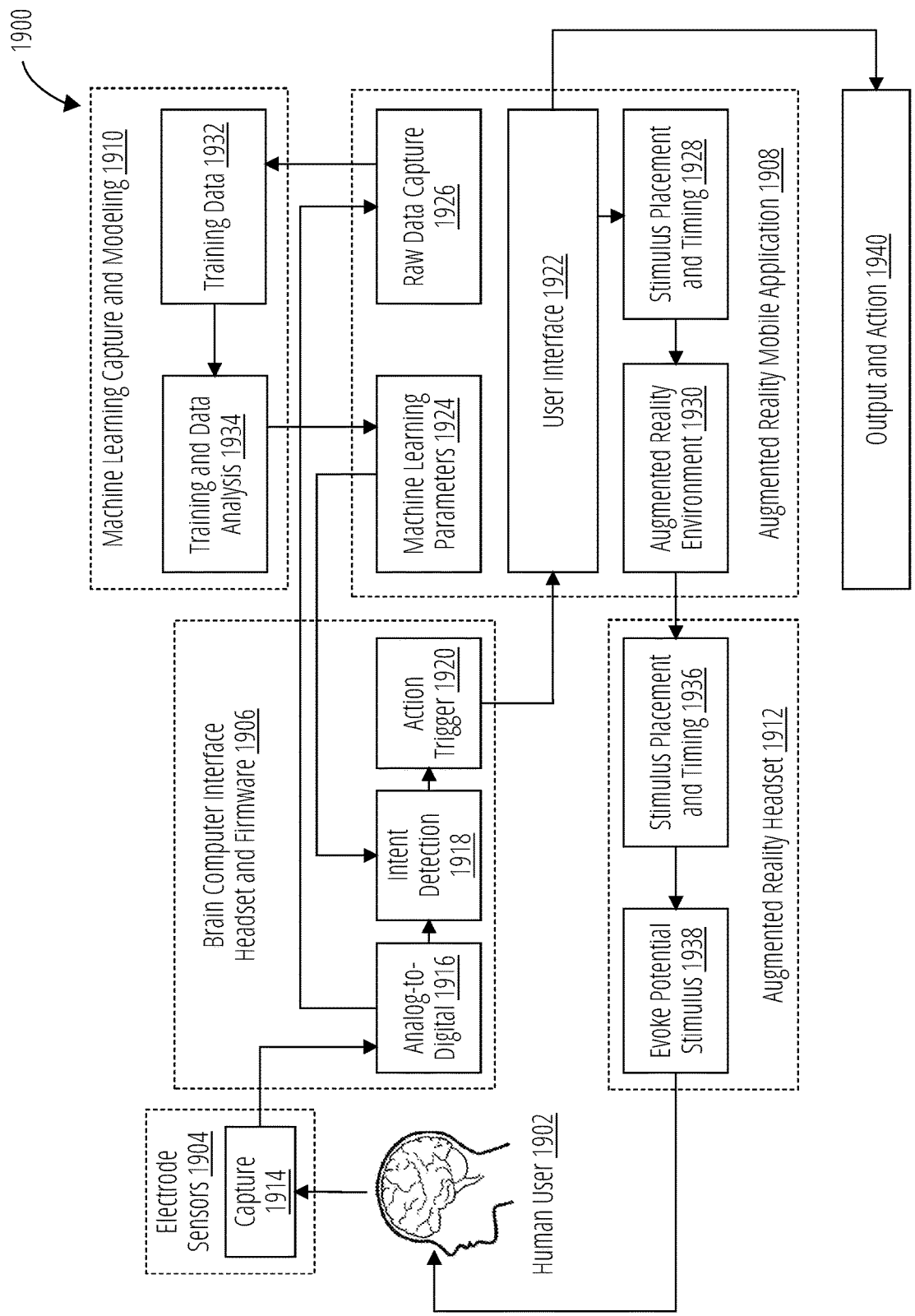
FIG. 19 illustrates a flow diagram 1900 in accordance with one embodiment.

FIG. 19 is a flow diagram 1900 showing a closed loop bio-signal data flow for a nonverbal multi-input and feedback device such as herein. It may be performed by inputs or a computer of the device. The flow diagram 1900 comprises a human user 1902, electrode sensors 1904, a brain computer interface headset and firmware 1906, an augmented reality mobile application 1908, machine learning capture and modeling 1910 that may be performed in an edge, peer, or cloud device, and an augmented reality headset 1912. The electrode sensors 1904 may capture 1914 data that is sent for analog-to-digital 1916 conversion. The digital signal may be used for intent detection 1918 resulting in an action trigger 1920 to a user interface 1922. The digital data may further be sent to raw data capture 1926, and may be used as training data 1932 for training and data analysis 1934. Training and data analysis 1934 may yield machine learning parameters 1924 which may be fed back for use in intent detection 1918. The user interface 1922 may determine stimulus placement and timing 1928, which may be used in the augmented reality environment 1930 created by the augmented reality mobile application 1908. The stimulus placement and timing 1936 resulting in the augmented reality headset 1912 and may evoke potential stimulus 1938 in the human user 1902. The user interface 1922 may also generate an output and action 1940.

The flow diagram 1900 includes computer stimulates visual, auditory and somatosensory cortex with evoked potentials; signal processing of real time streaming brain response; human controls computer based on mental fixation of stimulation frequencies; and system can determine different output or actions on behalf of the user for input data received via one or more sensors of the device. Flow diagram 1900 may apply to a user wearing any of the nonverbal multi-input and feedback devices and/or sensors herein. As a result of this being closed-loop biofeedback and sensory communication and control system that stimulates the brains senses of sight, sound, and touch and reads specific stimulation time-based frequencies, and tags them with metadata in real-time as the analog data is digitized, the user can rapidly learn how to navigate and interact with the system using their brain directly. This method of reinforcement learning is known in the rapid development process of the brain's pattern recognition abilities and the creation of neural plasticity to develop new neural connections based on stimulation and entrainment. This further enables the system to become a dynamic neural prosthetic extension of their physical and cognitive abilities. The merging of context awareness metadata, vocabulary, and output and action logic into the central application in addition to a universal interface for signal acquisition and data processing is what makes this system extremely special. Essentially, this system helps reduce the time latency between detecting cognitive intention and achieving the associated desired outcome, whether that be pushing a button, saying a word or controlling robots, prosthetics, smart home devices or other digital systems.

FIG. 20 is a flow diagram 2000 showing multimodal, multi-sensory system for communication and control 2002 for a nonverbal multi-input and feedback device such as herein. It may be performed by inputs or a computer of the device. The flow diagram 2000 comprises multimodal, multi-sensory systems for communication and control 2002 that includes wireless neck and head tracking 2004 and wireless brain tracking 2006. The multimodal, multi-sensory system for communication and control 2002 may further comprise central sensors 2008 for EEG, peripheral sensors 2010 such as EMG, EOG, ECG, and others, an analog to digital signal processor 2012 processing data from the central sensors 2008, and an analog to digital signal processor 2014 processing data from the peripheral sensors 2010. The analog to digital subsystem 2016 and sensor service subsystem 2018 manage output from the analog to digital signal processor 2012 and the analog to digital signal processor 2014, respectively. Output from the analog to digital subsystem 2016 may be sent to a storage subsystem 2060.

Outputs from the analog to digital subsystem 2016 and sensor service subsystem 2018 go to a collector subsystem 2020, which also receives a real-time clock 2022. The collector subsystem 2020 communicates with a recognizer 2024 for EEG data and a classifier 2026 for EMG, EOG, and ECG data, and data from other sensing. The collector subsystem 2020 further communicates to a wireless streamer 2028 and a serial streamer 2030 to interface with a miniaturized mobile computing system 2036 and a traditional workstation 2032, respectively. The traditional workstation 2032 and miniaturized mobile computing system 2036 may communicated with a cloud 2034 for storage or processing. The miniaturized mobile computing system 2036 may assist in wireless muscle tracking 2038 (e.g., EMG data) and wireless eye pupil tracking 2040.

A controller subsystem 2042 accepts input from a command queue 2044 which accepts input from a BT write callback 2050. The BT write callback 2050 may send commands 2046 to a serial read 2048. The controller subsystem 2042 may send output to the controller subsystem 2042 and a peripherals subsystem 2052. The peripherals subsystem 2052 generates audio feedback 2054, haptic feedback 2056, and OLED visual feedback 2058 for the user.

The flow diagram 2000 includes synchronizing signals from multiple biosensors including brain, body, eye and movement; processing multiple models concurrently for multi-sensory input; and directing and processing biofeedback through peripheral subsystems. Flow diagram 2000 may apply to a user wearing any of the nonverbal multi-input and feedback devices and/or sensors herein.

Figure 21:
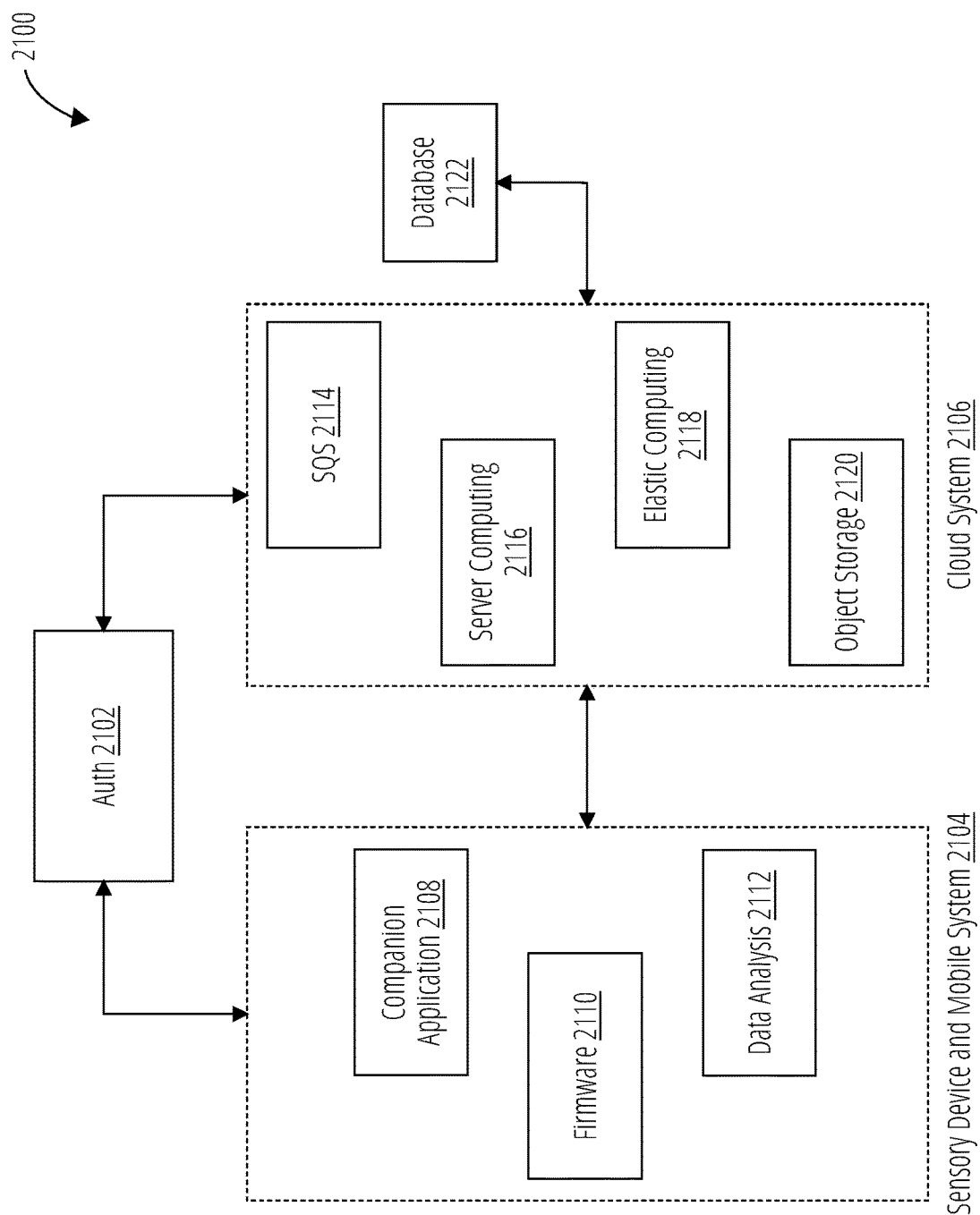
FIG. 21 illustrates a block diagram 2100 in accordance with one embodiment.

FIG. 21 is a block diagram 2100 showing an example of cloud processing for a nonverbal multi-input and feedback device such as herein. The block diagram 2100 comprises data authentication 2102, a sensory device and mobile system 2104, a cloud system 2106, and a database 2122. The data authentication 2102 module may be configured to authenticate data and communicate with the sensory device and mobile system 2104 and cloud system 2106. The sensory device and mobile system 2104 may include companion application 2108 and data collection, firmware 2110 and data collection, and data analysis 2112 or raw and processed data. The cloud system 2106 may comprise SQS message queuing 2114, server computing 2116 to analyze raw and process data, elastic computing 2118 to build, train, and test machine learning models, and object storage 2120 for persistent storage of biodata, machine learning, and metadata. The database 2122 stores associations and metadata and is in communication with the cloud system 2106.

Block diagram 2100 has the cloud system, the nonverbal multi-input device and an authorization system. Block diagram 2100 includes: machine learning processing signal data on device; metadata enrichment; push raw and processed data to cloud; cloud application building new models for devices; system updates devices remotely and wirelessly; secure and privacy compliant. This configuration is quite powerful but unassumingly simple in this block diagram.

Figure 22:
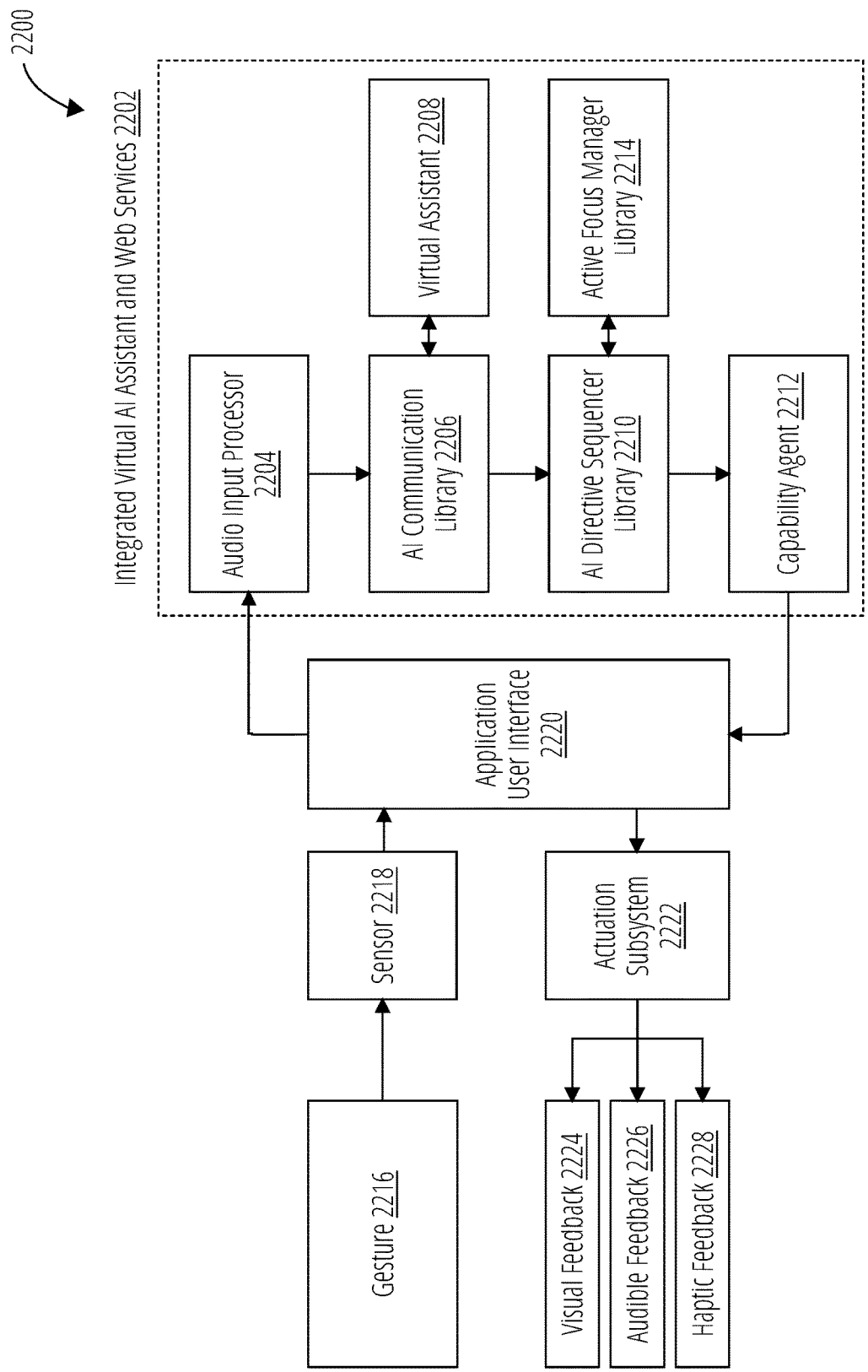
FIG. 22 illustrates a block diagram 2200 in accordance with one embodiment.

FIG. 22 is a block diagram 2200 showing an example of a system architecture for integrated virtual AI assistant and web services 2202 for a nonverbal multi-input and feedback device such as herein. The block diagram 2200 comprises integrated virtual AI assistant and web services 2202 which may include an audio input processor 2204, an AI communication library 2206, a virtual assistant 2208 such as Alexa, an AI directive sequencer library 2210, a capability agent 2212, and an active focus manager library 2214. A gesture 2216 from a user may be detected by a sensor 2218. An application user interface 2220 may process sensor data, and may send data to the audio input processor 2204. The capability agent 2212 may send data back to the application user interface 2220. The application user interface 2220 may signal an actuation subsystem 2222 to provide visual feedback 2224, audible feedback 2226, and haptic feedback 2228.

The block diagram 2200 includes: system manages intention signal acquisition, processing, language composition, and output; in the event where a user wants to send their intention to a virtual assistant (like Alexa, Siri). The blocks outside of the dashed border run on the sensory device, and currently, the blocks inside the dashed line are running in the cloud (e.g., represent a custom configuration for how to use the Alexa service in a cloud architecture.) It could also be possible that all of what's described here as in the cloud could run locally in the sensory device.

Figure 23:
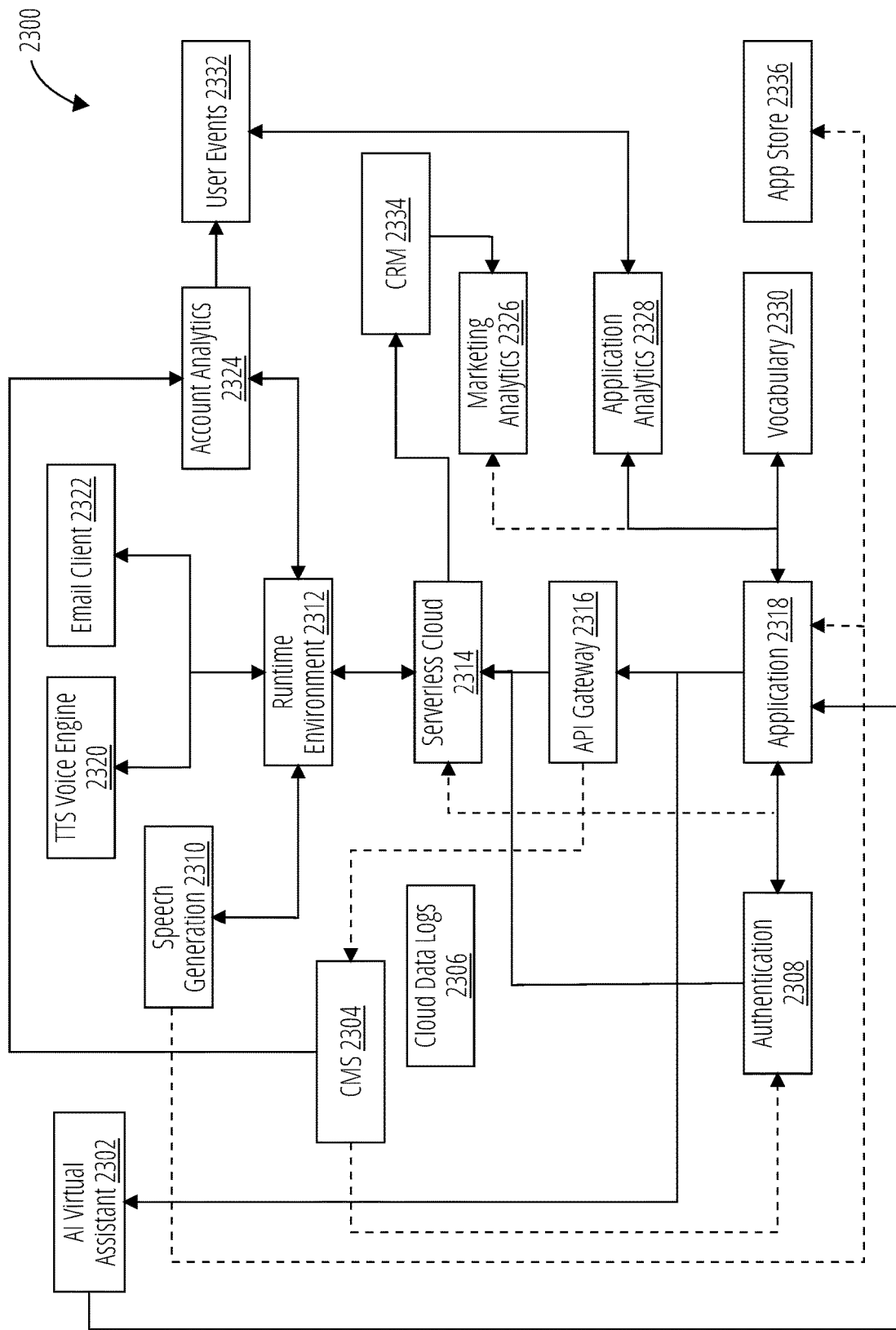
FIG. 23 illustrates a block diagram 2300 in accordance with one embodiment.

FIG. 23 is a block diagram 2300 showing an example of system operations for a nonverbal multi-input and feedback device such as herein. The block diagram 2300 comprises an AI virtual assistant 2302, such as Alexa, a content management system 2304, cloud data logs 2306, authentication 2308, speech generation 2310, a runtime environment 2312, a serverless cloud 2314, an API gateway 2316, an application 2318, a TTS voice engine 2320, an email client 2322, account analytics 2324, marketing analytics 2326, application analytics 2328, a vocabulary 2330, user events 2332, a customer relations management 2334, and an app store 2336.

Block diagram 2300 includes: system operation blocks including authentication. This is an example of the complexity of a system operating in the cloud. Everything in this figure is in the cloud, except for the application that is running on the sensory device. The augment/virtual reality application 2318 for the nonverbal multi-input and feedback device may interface with an authentication 2308 module, an API gateway 2316, a vocabulary 2330, application analytics 2328, AI virtual assistant 2302, and marketing analytics 2326. The AI virtual assistant 2302 may communicate back to the application 2318. The application 2318 may also be in direct communication with a serverless cloud 2314, or may communicate with the serverless cloud 2314 through the API gateway 2316. Authentication 2308 may also be in communication with the serverless cloud 2314. The API gateway 2316 further allows the application 2318 to communicate with the content management system 2304, which may be used to store cloud data logs 2306. The content management system 2304 may send data back to the application 2318 through the authentication 2308 module, which may act as a gateway to ensure security and content authorization. Finally, the content management system 2304 may provide data to an account analytics 2324 module. Account analytics 2324 may provide data to a user events 2332 module, which may in turn feed data to application analytics 2328.

The serverless cloud 2314 may allow communication with the runtime environment 2312 and the customer relations management 2334 module. The customer relations management 2334 may provide data for marketing analytics 2326. The runtime environment 2312 may interface with speech generation 2310, a TTS voice engine 2320, an email client 2322, and account analytics 2324. Speech generation 2310 may allow a user to access an app store 2336.

Figure 24A:
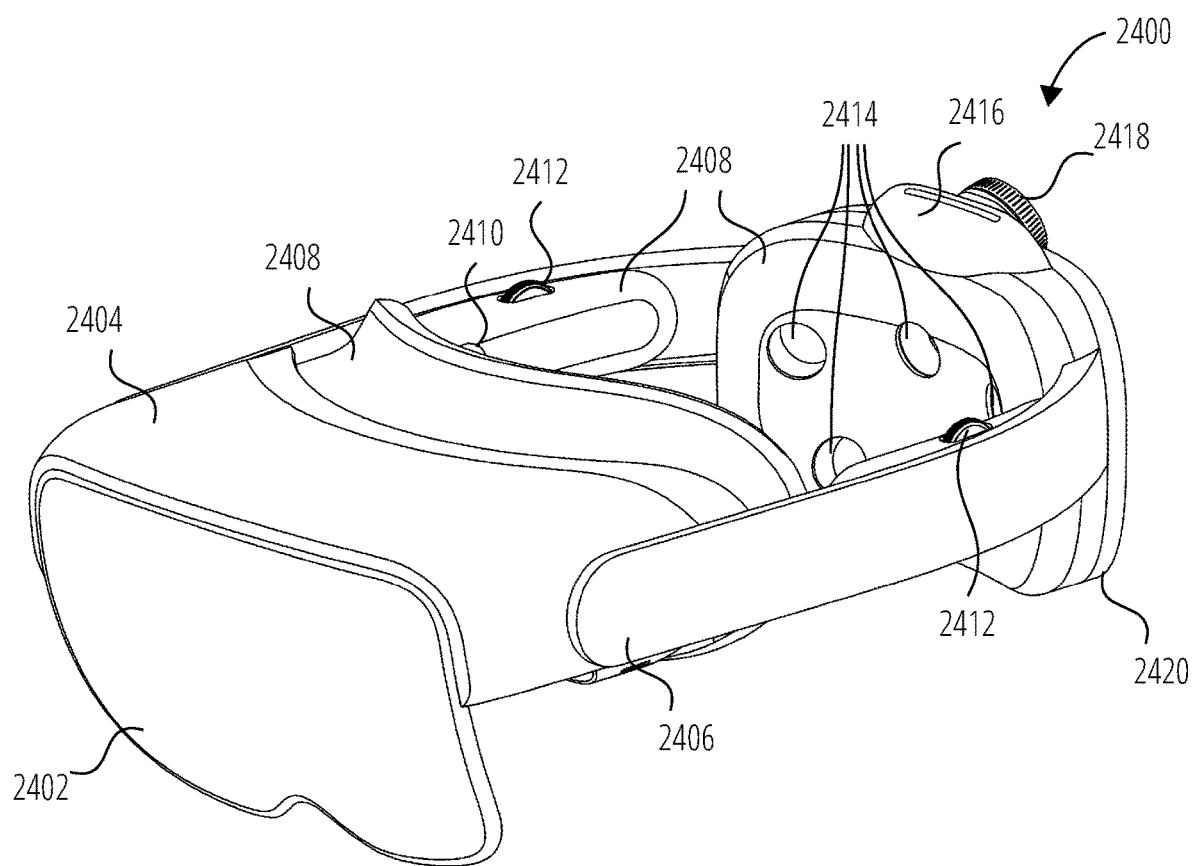
FIG. 24A illustrates an isometric view of a BCI headset system 2400 in accordance with one embodiment.

FIG. 24A illustrates an isometric view of a BCI headset system 2400 in accordance with one embodiment. The BCI headset system 2400 comprises an augmented reality display lens 2402, a top cover 2404, an adjustable strap 2406, a padding 2408, a ground/reference electrode 2410, a ground/reference electrode adjustment dial 2412, a biosensor electrodes 2414, a battery cell 2416, a fit adjustment dial 2418, and a control panel cover 2420.

Figure 24B:
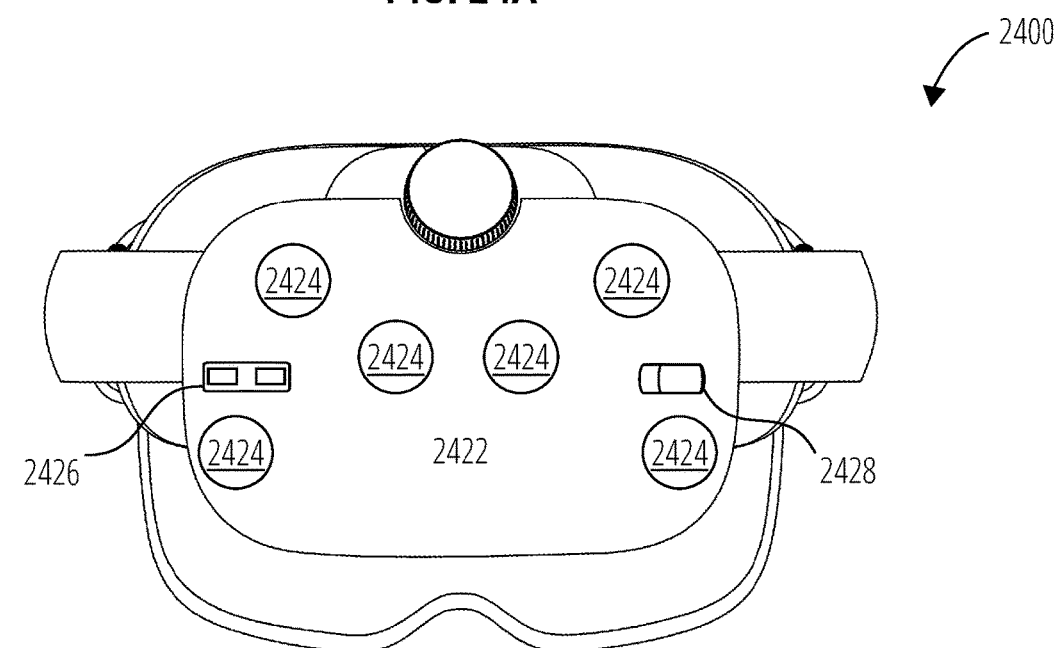
FIG. 24B illustrates arear view of a BCI headset system 2400 in accordance with one embodiment.
Figure 24C:
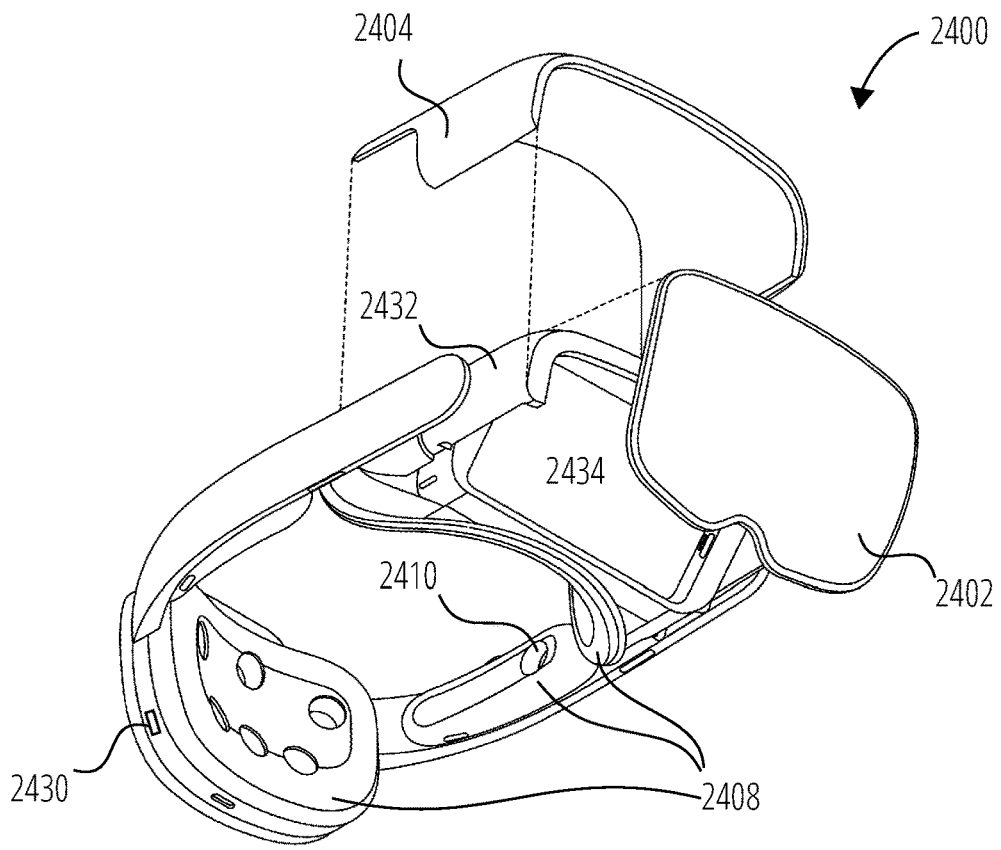
FIG. 24C illustrates an exploded view of a BCI headset system 2400 in accordance with one embodiment.

The augmented reality display lens 2402 may be removable from the top cover 2404 as illustrated in FIG. 24C. The augmented reality display lens 2402 and top cover 2404 may have magnetic portions that facilitate removably securing the augmented reality display lens 2402 to the top cover 2404. The augmented reality display lens 2402 may in one embodiment incorporate a frame around the lens material allowing the augmented reality display lens 2402 to be handled without depositing oils on the lens material.

The adjustable strap 2406 may secure the BCI headset system 2400 to a wearer's head. The adjustable strap 2406 may also provide a conduit for connections between the forward housing 2432 shown in FIG. 24C and the components located along the adjustable strap 2406 and to the rear of the BCI headset system 2400. Padding 2408 may be located at the front and rear of the BCI headset system 2400, as well as along the sides of the adjustable strap 2406, as illustrated. A fit adjustment dial 2418 at the rear of the BCI headset system 2400 may be used to tighten and loosen the fit of the BCI headset system 2400 by allowing adjustment to the adjustable strap 2406.

A snug fit of the BCI headset system 2400 may facilitate accurate readings from the ground/reference electrodes 2410 at the sides of the BCI headset system 2400, as illustrated here in FIG. 24A as well as in FIG. 24C. A snug fit may also facilitate accurate readings from the biosensor electrodes 2414 positioned at the back of the BCI headset system 2400. Further adjustment to these sensors may be made using the ground/reference electrode adjustment dials 2412 shown, as well as the biosensor electrode adjustment dials 2424 illustrated in FIG. 24B.

In addition to the padding 2408, biosensor electrodes 2414, and fit adjustment dial 2418 already described, the rear of the BCI headset system 2400 may incorporate a battery cell 2416, such as a rechargeable lithium battery pack. A control panel cover 2420 may protect additional features when installed, those features being further discussed with respect to FIG. 24B.

FIG. 24B illustrates a rear view of a BCI headset system 2400 in accordance with one embodiment. The control panel cover 2420 introduced in FIG. 24B is not shown in this figure, so that underlying elements may be illustrated. The BCI headset system 2400 further comprises a control panel 2422, a biosensor electrode adjustment dials 2424, an auxiliary electrode ports 2426, and a power switch 2428.

With the control panel cover 2420 removed, the wearer may access a control panel 2422 at the rear of the BCI headset system 2400. The control panel 2422 may include biosensor electrode adjustment dials 2424, which may be used to calibrate and adjust settings for the biosensor electrodes 2414 shown in FIG. 24A.

The control panel 2422 may also include auxiliary electrode ports 2426, such that additional electrodes may be connected to the BCI headset system 2400. For example, a set of gloves containing electrodes may be configured to interface with the BCI headset system 2400, and readings from the electrodes in the gloves may be sent to the BCI headset system 2400 wirelessly, or via a wired connection to the auxiliary electrode ports 2426.

The control panel 2422 may comprise a power switch 2428, allowing the wearer to power the unit on and off while the control panel cover 2420 is removed. Replacing the control panel cover 2420 may then protect the biosensor electrode adjustment dials 2424 and power switch 2428 from being accidentally contacted during use. In one embodiment, a power LED may be incorporated onto or near the power switch 2428 as an indicator of the status of unit power, e.g., on, off, battery low, etc.

FIG. 24C illustrates an exploded view of a BCI headset system 2400 in accordance with one embodiment. The BCI headset system 2400 further comprises a USB port 2430 in the rear of the BCI headset system 2400 as well as a forward housing 2432 which may be capable of holding a smart phone 2434. The USB port 2430 may in one embodiment be a port for a different signal and power connection type. The USB port 2430 may facilitate charging of the battery cell 2416, and may allow data transfer through connection to additional devices and electrodes.

The top cover 2404 may be removed from the forward housing 2432 as shown to allow access to the forward housing 2432, in order to seat and unseat a smart phone 2434. The smart phone 2434 may act as all or part of the augmented reality display. In a BCI headset system 2400 incorporating a smart phone 2434 in this manner, the augmented reality display lens 2402 may provide a reflective surface such that a wearer is able to see at least one of the smart phone 2434 display and the wearer's surroundings within their field of vision.

The top cover 2404 may incorporate a magnetized portion securing it to the forward housing 2432, as well as a magnetized lens reception area, such that the augmented reality display lens 2402 may, through incorporation of a magnetized frame, be secured in the front of the top cover 2404, and the augmented reality display lens 2402 may also be removable in order to facilitate secure storage or access to the forward housing 2432.

Figure 24D:
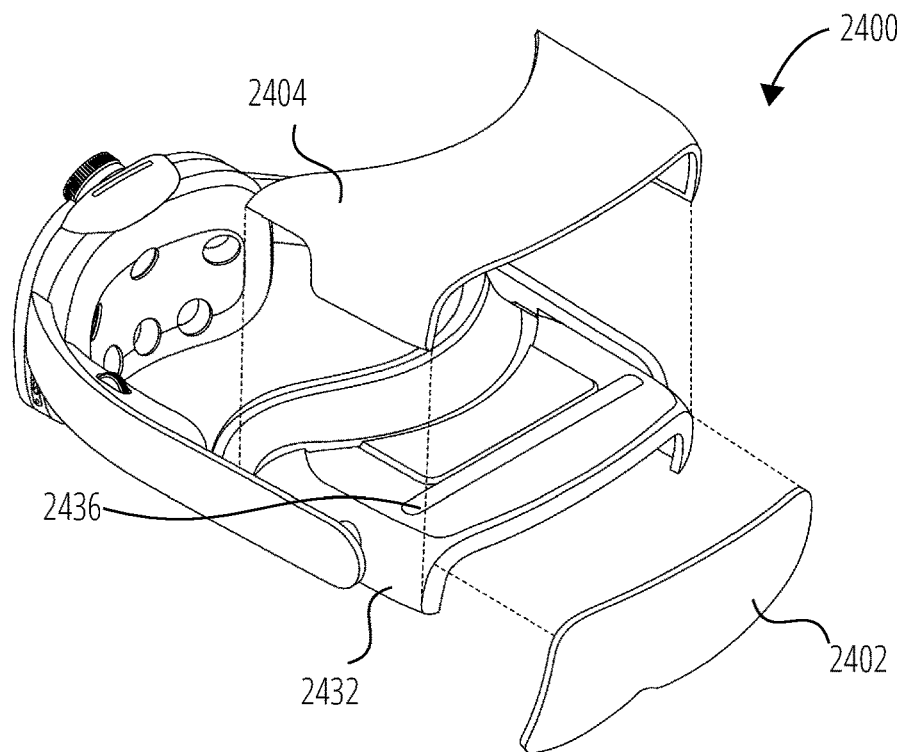
FIG. 24D illustrates an exploded view of a BCI headset system 2400 in accordance with one embodiment.

FIG. 24D illustrates an exploded view of a BCI headset system 2400 in accordance with one embodiment. The BCI headset system 2400 further comprises a smart phone slot 2436 in the forward housing 2432. When the augmented reality display lens 2402 and top cover 2404 are removed to expose the forward housing 2432 as shown, the smart phone slot 2436 may be accessed to allow a smart phone 2434 (not shown in this figure) to be inserted. In configurations where the BCI is an accessory that is bolted onto another AR/VR/Mix Reality system, the BCI headset system 2400 would not need one or more of the augmented reality display lens 2402, the top cover 2404, and the forward housing 2432.

LISTING OF DRAWING ELEMENTS

- 100 headset
- 102 PCB
- 104 strap
- 106 display
- 108 contoured sleeve
- 110 visual display source
- 200 disassembled BCI headset
- 202 pad
- 300 headset
- 302 cover
- 304 PCB
- 306 contoured sleeve
- 308 led
- 400 headset
- 402 sensor
- 404 additional sensors
- 406 sensor
- 408 sensor
- 410 contoured sleeve
- 412 PCB
- 414 slit
- 416 clasp
- 500 cross section of headset
- 502 contoured sleeve
- 504 sensor
- 506 third area
- 600 cross section of headset
- 602 second area
- 604 sensor
- 606 third area
- 608 first area
- 610 contoured sleeve
- 612 channel
- 700 cross section view of headset
- 702 contoured sleeve
- 704 second area
- 706 first area
- 708 sensor
- 710 battery
- 712 sensor
- 714 third area
- 716 led
- 800 method
- 802 block
- 804 block
- 806 block
- 808 block
- 810 block
- 812 block
- 900 device
- 902 printed circuit board
- 904 first area
- 906 second area
- 908 third area
- 910 analog front end
- 912 processing, analyzing and mapping
- 914 biofeedback
- 916 sensor header
- 918 EEG analog to digital
- 920 haptic controller
- 922 audio driver/amplifier
- 924 OLED
- 926 micro sd card
- 928 USB/TTL bridge
- 930 Bluetooth low energy module
- 932 microprocessor
- 934 power management module
- 1000 BCI+AR system
- 1002 sensor
- 1004 operating system
- 1006 user
- 1008 hardware
- 1100 BCI+AR environment
- 1102 human user
- 1104 sensor
- 1106 EEG analog to digital converter
- 1108 Audio/Video/Haptic Output
- 1110 processing
- 1112 augmented reality glasses
- 1114 strap
- 1116 BCI
- 1200 augmented reality device logic
- 1202 processing units
- 1204 CPU
- 1206 GPU
- 1208 WiFi
- 1210 Bluetooth
- 1212 speakers
- 1214 microphones
- 1216 memory
- 1218 logic
- 1220 graphics engine
- 1222 camera
- 1224 visual display
- 1226 vibration/haptic driver
- 1228 cloud
- 1230 Bluetooth keyboard
- 1300 block diagram of nonverbal multi-input and feedback device
- 1302 application
- 1304 multimodal input and intent detection
- 1306 context awareness
- 1308 vocabulary
- 1310 output and action
- 1312 touch
- 1314 bio-signals 1316 keyboard
1318 facial tracking
1320 eye and pupil tracking
1322 alternative inputs
1324 biometrics
1326 environment
1328 object recognition
1330 facial recognition
1332 voice recognition
1334 date and time
1336 history
1338 location
1340 proximity
1342 other metadata
1344 flat screen display
1346 augmented/virtual reality
1348 virtual AI assistant
1350 synthesized voice
1352 prosthetic device
1354 social media and messaging
1356 media consumption
1358 other output
1400 block diagram of a single framework of a nonverbal multi-input and feedback device
1402a sensor
1402b sensor
1402c sensor
1402d sensor
1402e sensor
1402f sensor
1404 input gesture
1406 context awareness
1408 machine learning
1410 output expression
1412 destination
1414 touch
1416 movement
1418 mental
1420 glances
1422 audible
1424 breath
1426 time synchronization
1428 configure data sources
1430 configure data processing parameters
1432 configure timing
1434 metadata tagging
1436 acquire analog data streams
1438 convert to digital data streams
1440 analyze data streams
1442 execute digital operations for actuation
1444 text
1446 symbol
1448 color
1450 image
1452 sound
1454 vibration
1456 mobile
1458 wearable 1
1460 wearable 2
1462 implant 1
1464 implant 2
1466 prosthetic 1
1500 block diagram of nonverbal multi-input and feedback device
1502 analog input
1504 sensors
1506 processing
1508 digital output
1510 output methods
1512 historical data
1514 learning system
1516 network
1518 personalization settings
1520 metadata
1522 application
1524 primary and secondary languages
1526 visual
1528 audible
1530 written
1602 head motion analog input
1604 headset with head motion detection sensors
1606 user selects options through head motion
1608 application creates output based on the user's selected options
1610 condition that system detects the user is away from home
1612 send output to a caregiver via text message
1702 user wears an EEG-based brain-computer interface headset
1704 electrodes that are contacting the scalp
1706 streaming analog data can be acquired from the brainwave activity
1708 set of words to choose from
1710 phrase they've composed
1802 augmented reality headset combined with a brain computer interface
1804 head motion analog input and brainwave activity
1806 set of words to choose from
1808 phrase they've composed
1900 flow diagram
1902 human user
1904 electrode sensors
1906 brain computer interface headset and firmware
1908 augmented reality mobile application
1910 machine learning capture and modeling
1912 augmented reality headset
1914 capture
1916 analog-to-digital
1918 intent detection
1920 action trigger
1922 user interface
1924 machine learning parameters
1926 raw data capture
1928 stimulus placement and timing
1930 augmented reality environment
1932 training data
1934 training and data analysis
1936 stimulus placement and timing
1938 evoke potential stimulus
1940 output and action
2000 flow diagram
2002 multimodal, multi-sensory system for communication and control
2004 wireless neck and head tracking
2006 wireless brain tracking
2008 central sensors
2010 peripheral sensors
2012 analog to digital signal processor
2014 analog to digital signal processor
2016 analog to digital subsystem
2018 sensor service subsystem
2020 collector subsystem
2022 real-time clock
2024 recognizer 2026 classifier
2028 wireless streamer
2030 serial streamer
2032 traditional workstation
2034 cloud
2036 miniaturized mobile computing system
2038 wireless muscle tracking
2040 wireless eye pupil tracking
2042 controller subsystem
2044 command queue
2046 command
2048 serial read
2050 BT write callback
2052 peripherals subsystem
2054 audio feedback
2056 haptic feedback
2058 OLED visual feedback
2060 storage subsystem
2100 block diagram
2102 data authentication
2104 sensory device and mobile system
2106 cloud system
2108 companion application
2110 firmware
2112 data analysis
2114 SQS message queuing
2116 server computing
2118 elastic computing
2120 object storage
2122 database
2200 block diagram
2202 integrated virtual AI assistant and web services
2204 audio input processor
2206 AI communication library
2208 virtual assistant
2210 AI directive sequencer library
2212 capability agent
2214 active focus manager library
2216 gesture
2218 sensor
2220 application user interface
2222 actuation subsystem
2224 visual feedback
2226 audible feedback
2228 haptic feedback
2300 block diagram
2302 AI virtual assistant
2304 content management system
2306 cloud data logs
2308 authentication
2310 speech generation
2312 runtime environment
2314 serverless cloud
2316 API gateway
2318 application
2320 TTS voice engine
2322 email client
2324 account analytics
2326 marketing analytics
2328 application analytics
2330 vocabulary
2332 user events
2334 customer relations management
2336 app store
2400 BCI headset system
2402 augmented reality display lens
2404 top cover
2406 adjustable strap
2408 padding
2410 ground/reference electrode
2412 ground/reference electrode adjustment dial
2414 biosensor electrodes
2416 battery cell
2418 fit adjustment dial
2420 control panel cover
2422 control panel
2424 biosensor electrode adjustment dials
2426 auxiliary electrode ports
2428 power switch
2430 USB port
2432 forward housing
2434 smart phone
2436 smart phone slot Within this disclosure, different entities (which may variously be referred to as "units," "circuits," other components, etc.) may be described or claimed as "configured" to perform one or more tasks or operations. This formulation—[entity] configured to [perform one or more tasks]—is used herein to refer to structure (i.e., something physical, such as an electronic circuit). More specifically, this formulation is used to indicate that this structure is arranged to perform the one or more tasks during operation. A structure can be said to be "configured to" perform some task even if the structure is not currently being operated. A "credit distribution circuit configured to distribute credits to a plurality of processor cores" is intended to cover, for example, an integrated circuit that has circuitry that performs this function during operation, even if the integrated circuit in question is not currently being used (e.g., a power supply is not connected to it). Thus, an entity described or recited as "configured to" perform some task refers to something physical, such as a device, circuit, memory storing program instructions executable to implement the task, etc. This phrase is not used herein to refer to something intangible.

The term "configured to" is not intended to mean "configurable to." An unprogrammed FPGA, for example, would not be considered to be "configured to" perform some specific function, although it may be "configurable to" perform that function after programming.

Reciting in the appended claims that a structure is "configured to" perform one or more tasks is expressly intended not to invoke 35 U.S.C. § 112(f) for that claim element. Accordingly, claims in this application that do not otherwise include the "means for" [performing a function] construct should not be interpreted under 35 U.S.C § 112(f).

As used herein, the term "based on" is used to describe one or more factors that affect a determination. This term does not foreclose the possibility that additional factors may affect the determination. That is, a determination may be solely based on specified factors or based on the specified factors as well as other, unspecified factors. Consider the phrase "determine A based on B." This phrase specifies that B is a factor that is used to determine A or that affects the determination of A. This phrase does not foreclose that the determination of A may also be based on some other factor, such as C. This phrase is also intended to cover an embodiment in which A is determined based solely on B. As used herein, the phrase "based on" is synonymous with the phrase "based at least in part on."

As used herein, the phrase "in response to" describes one or more factors that trigger an effect. This phrase does not foreclose the possibility that additional factors may affect or otherwise trigger the effect. That is, an effect may be solely in response to those factors, or may be in response to the specified factors as well as other, unspecified factors. Consider the phrase "perform A in response to B." This phrase specifies that B is a factor that triggers the performance of A. This phrase does not foreclose that performing A may also be in response to some other factor, such as C. This phrase is also intended to cover an embodiment in which A is performed solely in response to B.

As used herein, the terms "first," "second," etc. are used as labels for nouns that they precede, and do not imply any type of ordering (e.g., spatial, temporal, logical, etc.), unless stated otherwise. For example, in a register file having eight registers, the terms "first register" and "second register" can be used to refer to any two of the eight registers, and not, for example, just logical registers 0 and 1.

When used in the claims, the term "or" is used as an inclusive or and not as an exclusive or. For example, the phrase "at least one of x, y, or z" means any one of x, y, and z, as well as any combination thereof.

The apparatuses, methods, and systems in this disclosure are described in the preceding on the basis of several preferred embodiments. Different aspects of different variants are considered to be described in combination with each other such that all combinations that upon reading by a skilled person in the field on the basis of this document may be regarded as being read within the concept of the disclosure. The preferred embodiments do not limit the extent of protection of this document.

Having thus described embodiments of the present disclosure of the present application in detail and by reference to illustrative embodiments thereof, it will be apparent that modifications and variations are possible without departing from the scope of the present disclosure.

What is claimed is:

1. A method of determining and responding to a user's event-related potential, the method comprising:
    simultaneously generating two or more selectable target stimuli with a stimulus device worn by the user, wherein the stimulus device generates at least one of an audio stimulation, a visual stimulation, and a tactile stimulation for each of the two or more selectable target stimuli, and
    wherein there is at least one known response bio-signal associated with each of the two or more selectable target stimuli;
    detecting the at least one known response bio-signal with a wearable biosensor worn by the user, wherein the wearable biosensor comprises at least two sensors for reading bio-signals from the user, the bio-signals comprising at least one of:
    EEG (Electroencephalography);
    ECG (Electrocardiography);
    functional near infrared spectroscopy (fNIRS);
    Magnetoencephalography (MEG);
    EMG (Electromyography);
    EOG (Electroocculography);
    Time-Domain variants (TD-) of at least one of: a visually evoked potential, an audio evoked potential, a haptic evoked potential, a motion evoked potential; and
    other bio-signals from multiple sources attached to other body parts other than a user's head;
    determining using at least one processing module that the user's event-related potential is in response to at least one of the two or more selectable target stimuli based at least on detecting the at least one known response bio-signal;
    mapping using the at least one processing module the at least one known response bio-signal to a digital command based on the user's event-related potential, wherein the digital command includes at least one of instructions for triggering a visual effect, instructions for triggering an audible effect, and instructions for triggering a tactile effect;
    sending the digital command to an integrated virtual AI assistant, selected by a capability agent, configured to perform an action based on the digital command and a user's context as interpreted by the integrated virtual AI assistant;
    sending the digital command to at least one biofeedback device that produces at least one of the visual effect, the audible effect, and the tactile effect;
    triggering at least one of the visual effect, the audible effect, and the tactile effect to provide feedback to the user based on the user's event-related potential.

2. The method of claim 1, wherein the wearable biosensor is configured within a fully self-contained brain computer interface in a wireless headset.

3. The method of claim 1, wherein the stimulus device is configured within a fully self-contained brain computer interface in a wireless headset.

4. The method of claim 1, wherein the at least one biofeedback device is configured within a fully self-contained brain computer interface in a wireless headset.

5. The method of claim 1, wherein the stimulus device and the at least one biofeedback device are configured as a single device.

6. The method of claim 1, wherein the user's event-related potential indicates at least one of user attention to the at least one of the two or more selectable target stimuli and user inattention to the two or more selectable target stimulus.

7. The method of claim 1, further comprising:
    determining the user's event-related potential is in response to the at least one of the two or more selectable target stimuli further based on metadata from other sensors and data sources in communication with the at least one processing module.

8. The method of claim 1, wherein the at least one biofeedback device is configured to stimulate at least one of a user's central nervous system and peripheral nervous system.

9. The method of claim 1, wherein the processing module has different modes that include at least one of a raw mode, a simmer mode, a cooked mode, a human interface device-keyboard mode, and combinations thereof.

10. The method of claim 9, wherein metadata from other sensors and data sources is appended to raw data, cooked data, and simmer data in order for the processing module to alter the digital command that is sent to execute on the at least one biofeedback device.

11. A system for determining and responding to a user's event-related potential, the system comprising:
    a stimulus device, wherein the stimulus device simultaneously generates at least one of an audio stimulation, a visual stimulation, and a tactile stimulation for each of two or more selectable target stimuli;
    a wearable biosensor comprising at least two sensors for reading bio-signals from the user, the bio-signals comprising at least one of:
    EEG (Electroencephalography);
    ECG (Electrocardiogra
    functional near infrared spectroscopy (fNIRS);
    Magnetoencephalography (MEG);
    EMG (Electromyography);

EOG (Electrooculography);
Time-Domain variants (TD-) of at least one of: a visually evoked potential, an audio evoked potential, a haptic evoked potential, a motion evoked potential; and other bio-signals from multiple sources attached to other body parts other than a user's head;
at least one biofeedback device that produces at least one of a visual effect, a audible effect, and a tactile effect;
at least one processing module; and
a memory storing instructions that, when executed by the at least one processing module, configure the system to:
simultaneously generate the two or more selectable target stimuli with the stimulus device worn by the user, wherein there is at least one known response bio-signal associated with each of the two or more selectable target stimuli;
detect the at least one known response bio-signal with the wearable biosensor worn by the user;
determine that the user's event-related potential is in response to at least one of the two or more selectable target stimuli based at least on detecting the at least one known response bio-signal;
map the at least one known response bio-signal to a digital command based on the user's event-related potential, wherein the digital command includes at least one of instructions for triggering the visual effect, instructions for triggering the audible effect, and instructions for triggering the tactile effect;
send the digital command to an integrated virtual AI assistant, selected by a capability agent, configured to perform an action based on the digital command and a user's context as interpreted by the integrated virtual AI assistant;
send the digital command to the at least one biofeedback device;
trigger at least one of the visual effect, the audible effect, and the tactile effect to provide feedback to the user based on the user's event-related potential.

12. The system of claim 11, wherein the wearable biosensor is configured within a fully self-contained brain computer interface in a wireless headset.

13. The system of claim 11, wherein the stimulus device is configured within a fully self-contained brain computer interface in a wireless headset.

14. The system of claim 11, wherein the at least one biofeedback device is configured within a fully self-contained brain computer interface in a wireless headset.

15. The system of claim 11, wherein the stimulus device and the at least one biofeedback device are configured as a single device.

16. The system of claim 11, wherein the user's event-related potential indicates at least one of user attention to the at least one of the two or more selectable target stimuli and user inattention to the two or more selectable target stimuli.

17. The system of claim 11, further comprising other sensors and data sources in communication with the at least one processing module, wherein the instructions further configure the apparatus to:
determine the user's event-related potential is in response to the at least one of the two or more selectable target stimuli further based on metadata from the other sensors and data sources.

18. The system of claim 11, wherein the at least one biofeedback device is configured to stimulate at least one of a user's central nervous system and peripheral nervous system.

19. The system of claim 11, wherein the processing module has different modes that include at least one of a raw mode, a simmer mode, a cooked mode, a human interface device-keyboard mode, and combinations thereof.

20. The system of claim 19, further comprising other sensors and data sources in communication with the at least one processing module, wherein metadata from the other sensors and data sources is appended to raw data, cooked data, and simmer data in order for the processing module to alter the digital command that is sent to execute on the at least one biofeedback device.

21. A method of enabling a user to interact with their environment using a wearable stimulus device, the method comprising:
providing the user with two or more selectable communication options using the wearable stimulus device worn by the user,
wherein the wearable stimulus device generates at least two stimulation effects, at least one for each of the two or more selectable communication options,
wherein each of the at least two stimulation effects are at least one of an audio stimulation, a visual stimulation, and a tactile stimulation, and
wherein at least one known response bio-signal is associated with each of the at least two stimulation effects;
detecting, with a wearable biosensor worn by the user, the at least one known response bio-signal, wherein the wearable biosensor communicates with at least one processing module;
mapping, using the at least one processing module, the at least one known response bio-signal to a digital command;
sending the digital command to at least one output action device,
wherein the at least one output action device is configured to perform an action based on the digital command and a user's context, and
wherein the at least one output action device includes one of a natural language system, an integrated virtual AI assistant, selected by a capability agent, configured to interpret the user's context, a synthesized voice, and a prosthetic device; and
recording the digital command for future use.

22. The method of claim 21, further comprising:
sending the digital command to at least one biofeedback device, wherein the at least one biofeedback device produces at least one of a visual effect, an audible effect, and a tactile effect; and
triggering the at least one of the visual effect, the audible effect, and the tactile effect to provide feedback to the user based on the digital command.

23. The method of claim 21, wherein the action performed by the output action device enables the user to interact verbally with their environment.

24. The method of claim 21, wherein the at least one output action device includes an augmented reality/virtual reality display.

25. The method of claim 24 wherein at least a portion of the at least one known response bio-signal is detected from data captured by a wearable head strap that is an accessory to the augmented reality/virtual reality display.

26. The method of claim 21, wherein the at least one known response bio-signal is an evoked potential.

27. The method of claim 21, wherein some portion of the at least one output action device utilizes a processing device that is connected to the wearable stimulus device over a network.

28. The method of claim 21, wherein the at least one processing module further incorporates context awareness input into at least one of the two or more selectable communication options and the digital command.

29. The method of claim 1, wherein the integrated virtual AI assistant generates a communication output that instructs at least one of an augmented reality/virtual reality display, a natural language system, a synthesized voice, and a prosthetic device to perform the action based on the digital command that enables the user to interact with their environment.

30. The method of claim 11, wherein the integrated virtual AI assistant generates a communication output that instructs at least one of an augmented reality/virtual reality display, a natural language system, a synthesized voice, and a prosthetic device to perform the action based on the digital command that enables the user to interact with their environment.

31. The method of claim 1, further comprising sending the digital command to web services.

\* \* \* \* \*